(12) United States Patent
Gribble et al.

(10) Patent No.: US 6,552,075 B2
(45) Date of Patent: Apr. 22, 2003

(54) THERAPEUTIC COMPOUNDS AND METHODS OF USE

(75) Inventors: Gordon W. Gribble, Norwich, VT (US); Tadashi Honda, Hanover, NH (US); Michael B. Sporn, Tunbridge, VT (US); Nanjoo Suh, Hanover, NH (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 09/927,081

(22) Filed: Aug. 9, 2001

(65) Prior Publication Data

US 2002/0042535 A1 Apr. 11, 2002

Related U.S. Application Data

(62) Division of application No. 09/335,003, filed on Jun. 17, 1999, now Pat. No. 6,326,507

(60) Provisional application No. 60/090,053, filed on Jun. 19, 1998.

(51) Int. Cl.$^7$ .................. A61K 31/275; A61K 31/19
(52) U.S. Cl. ...................... 514/522; 514/557
(58) Field of Search .................. 558/415, 423; 514/527, 557; 560/55

(56) References Cited

U.S. PATENT DOCUMENTS 4,395,423 A * 7/1983 Neumann .................. 424/304

* cited by examiner

*Primary Examiner*—Robert W. Ramsuer
*Assistant Examiner*—Ebenezer Sackey
(74) *Attorney, Agent, or Firm*—Fulbright & Jaworski

(57) ABSTRACT

Compounds and methods useful for chemopreventative treatment of diseases such as cancer, Alzheimer's disease, Parkinson's disease, inflammatory bowel diseases, and multiple sclerosis.

61 Claims, 11 Drawing Sheets

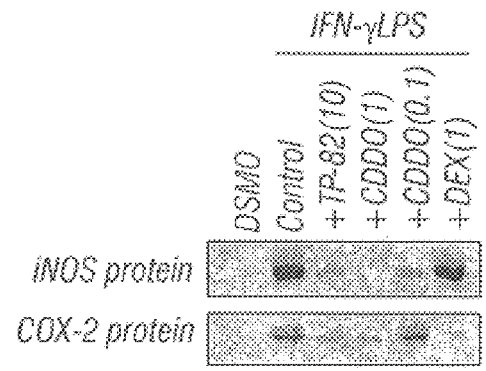 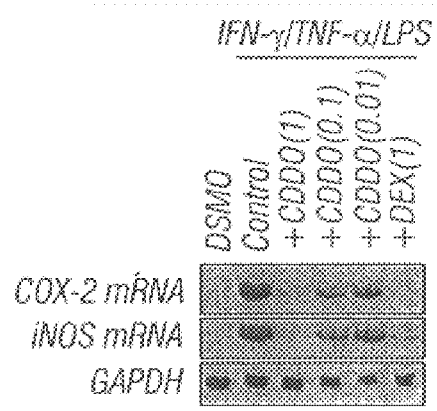
FIG. 14A  FIG. 14B
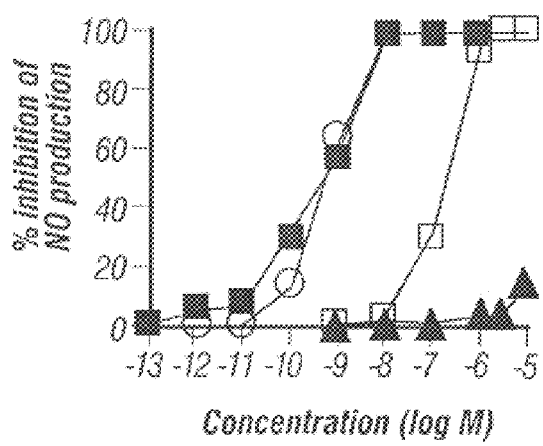 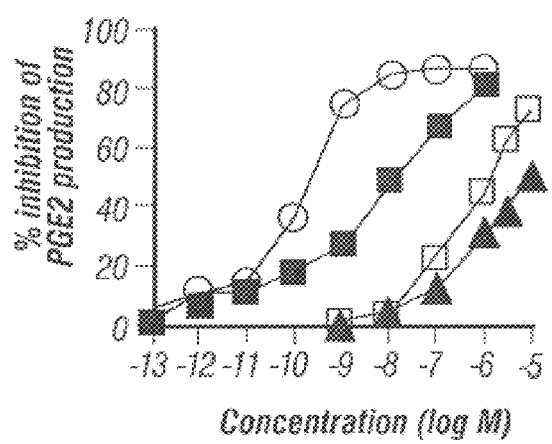
FIG. 14C
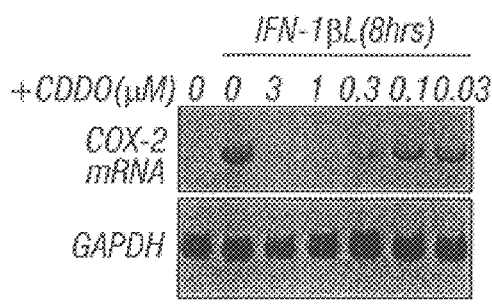 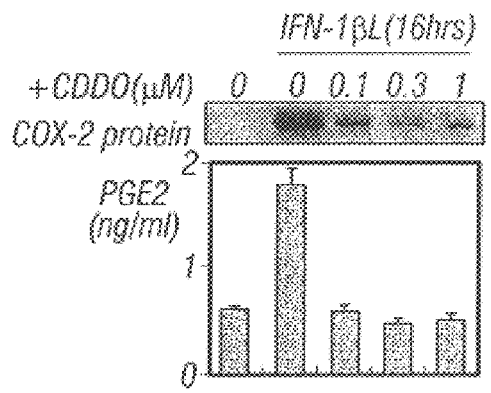
FIG. 14D  FIG. 14E

THERAPEUTIC COMPOUNDS AND METHODS OF USE

This is a divisional of application Ser. No. 09/335,003, filed Jun. 17, 1999, now U.S. Pat. No. 6,326,507 which is related to and claims the benefit of priority to U.S. Provisional Application No. 60/090,053 filed Jun. 19, 1998, the entire contents of which are incorporated herein by reference. Additionally, all patents, published patent applications, and other references cited throughout this specification are hereby incorporated by reference in their entireties.

The invention disclosed herein was made with the support of the U.S. Government under NIH Grants CA-23108, RO1 CA 54494, RO1 CA 62275, KO1 CA 75154, NS 28767, and DOD/AMRD Award 1796-1-6163. Accordingly, the U.S. Government may have certain rights in this invention.

BACKGROUND OF THE INVENTION

The present invention relates to compounds which have been found to be useful for prevention or treatment of diseases such as cancer, Alzheimer's disease, Parkinson's disease, multiple sclerosis, rheumatoid arthritis, and other inflammatory diseases.

One of the major needs in cancer prevention is the development of effective and safe new agents for chemoprevention. In particular, there is a need for chemopreventative agents targeted at mechanisms known to be involved in the process of carcinogenesis. In recent years, there has been a resurgence of interest in the study of mechanisms of inflammation that relate to carcinogenesis and in the use of such mechanisms as the basis for development of new chemopreventative agents.

The concept that inflammation and carcinogenesis are related phenomena has been the subject of many studies that have attempted to link these two processes in a mechanistic fashion (Sporn and Roberts, 1986; Ohshima and Bartsch, 1994). The enzymes that mediate the constitutive synthesis of NO and prostaglandins from arginine and arachidonate, respectively, have relative little significance for either inflammation or carcinogenesis. In contrast, inducible nitric oxide synthase (iNOS) and inducible cycloxygenase (COX-2) both have critical roles in the response of tissues to injury or infectious agents (Moncada et al., 1991; Nathan and Xie, 1994; Siebert and Masferrer, 1994; Tamir and Tannebaum, 1996). These inducible enzymes are essential components of the inflammatory process, the ultimate repair of injury, and carcinogenesis. While physiological activity of iNOS and COX-2 may provide a definite benefit to the organism, aberrant or excessive expression of either iNOS or COX-2 has been implicated in the pathogenesis of many disease processes, particularly in chronic degeneration of the central nervous system, carcinogenesis, septic shock, cardiomyopathy, and rheumatoid arthritis.

Triterpenoids, biosynthesized in plants by the cyclization of squalene, are used for medicinal purposes in many Asian countries; and some, like ursolic and oleanolic acids, are known to be anti-inflammatory and anti-carcinogenic (Huang et al., 1994; Nishino et al., 1988). However, the biological activity of these naturally occurring molecules is relatively weak, and therefore the synthesis of new analogs to enhance their potency was undertaken (Honda et al., 1997; Honda et al., 1998). It was previously reported that several such synthetic analogs can suppress the de novo formation of iNOS and COX-2 in macrophages that have been stimulated by IFN-γ or LPS (Suh et al., 1998). The role of both iNOS and COX-2 as enhancers of carcinogenesis in many organs is receiving increasing attention (Ohshima et al., 1994; Tamir et al., 1996; Takahashi et al., 1997; Ambs et al., 1998; Tsujii et al., 1998; Oshima et al., 1996; Hida et al., 1998; Huang et al., 1998); suppression of either the synthesis or the activity of these enzymes is therefore a target for chemoprevention (Oshima et al., 1998; Kawamori et al., 1998). Agents which induce differentiation or suppress proliferation of premalignant or malignant cells represent yet another mechanistic approach to chemoprevention, as well as to chemotherapy, of cancer.

SUMMARY OF THE INVENTION

The present invention provides methods and compositions for the prevention or treatment of diseases such as cancer, Alzheimer's disease, Parkinson's disease, and multiple sclerosis. The methods of the invention involve administering to a subject a therapeutic compound of the formula:

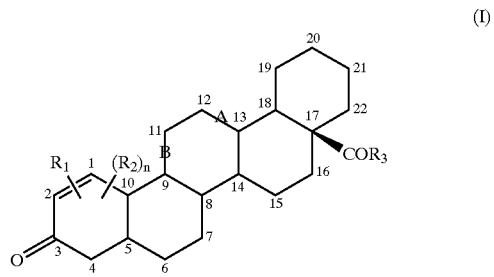

wherein A or B is a single or double bond and $C_{11}$ or $C_{12}$ have substituted thereon =X which is an organic or inorganic moiety; $R_1$ is an organic or inorganic moiety which may be substituted anywhere on the six-membered ring denoted by positions 1 through 10; $R_2$ and $R_3$ are hydrogen or organic or inorganic moieties, wherein an $R_2$ group may be substituted anywhere on the structure represented in the formula; and n is a number from 0 to 100.

The invention further relates to therapeutic compositions and methods of their use having the formula

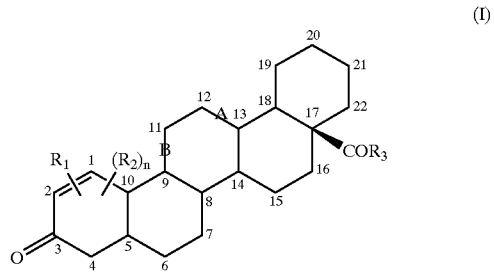

wherein either A or B is a double bond such that when A is a double bond, $C_{11}$ has substituted thereon =X which is an organic or inorganic moiety and when B is a double bond, $C_{12}$ has substituted thereon =X; $R_1$ is an organic or inorganic moiety which may be substituted anywhere on the six-membered ring denoted by positions 1 through 10; $R_2$ and $R_3$ are hydrogen or organic or inorganic moieties, wherein an $R_2$ group may be substituted anywhere on the structure represented in formula (I); and n is a number from 0 to 100).

Accordingly, in an embodiment the compositions and methods of the invention are useful for prevention or treatment of disorders such as cancer; neurodegenerative diseases (NDDs) such as Parkinson's disease (PD), Alzheimer's disease (AD), multiple sclerosis (MS), and amyotrophic lateral sclerosis (ALS); inflammatory diseases, e.g., inflammatory bowel diseases such as Crohn's disease and ulcerative colitis; and rheumatoid arthritis (RA). The methods of the invention can be used therapeutically to prevent or treat such conditions in a subject. The methods are based, at least in part, on the discovery that the presently disclosed compounds have been found to suppress transcription or translation of iNOS and COX-2 genes, the overexpression of which is linked with excess NO and/or prostaglandin formation.

In a further aspect the invention relates to triterpenoid compositions effective for modulating interferon-γ (IFN-γ)-induced NO production in macrophages, said composition having an $IC_{50}$ value of at least less than 0.6 μM, preferably less than 0.001 μM.

In another aspect a method of preventing or treating a disorder characterized by overexpression of iNOS or COX-2 genes is presented, comprising administering to a subject a pharmaceutically effective amount of a composition of formula (I), such that the disorder is prevented or treated. Such disorders include cancer; neurodegenerative diseases such as Parkinson's disease, Alzheimer's disease, multiple sclerosis, and amyotrophic lateral sclerosis; and rheumatoid arthritis.

In a further aspect a method of modulating transcription or translation of iNOS or COX-2 genes in a subject comprises administering to a subject a pharmaceutically effective amount of a composition of formula (I), such that the transcription or translation of iNOS or COX-2 genes is modulated.

In yet another aspect a method of modulating excessive nitric oxide or prostaglandin formation in a subject is presented, comprising administering to a subject a pharmaceutically effective amount of a composition of formula (I), such that nitric oxide or prostaglandin formation is modulated.

BRIEF DESCRIPTION OF THE DRAWINGS

FIGS. 14(A)–(E) shows inhibitory effects of triterpenoids on induction of iNOS and COX-2 in mouse macrophages and human colon fibroblasts.

DETAILED DESCRIPTION OF THE INVENTION

Figure 1:
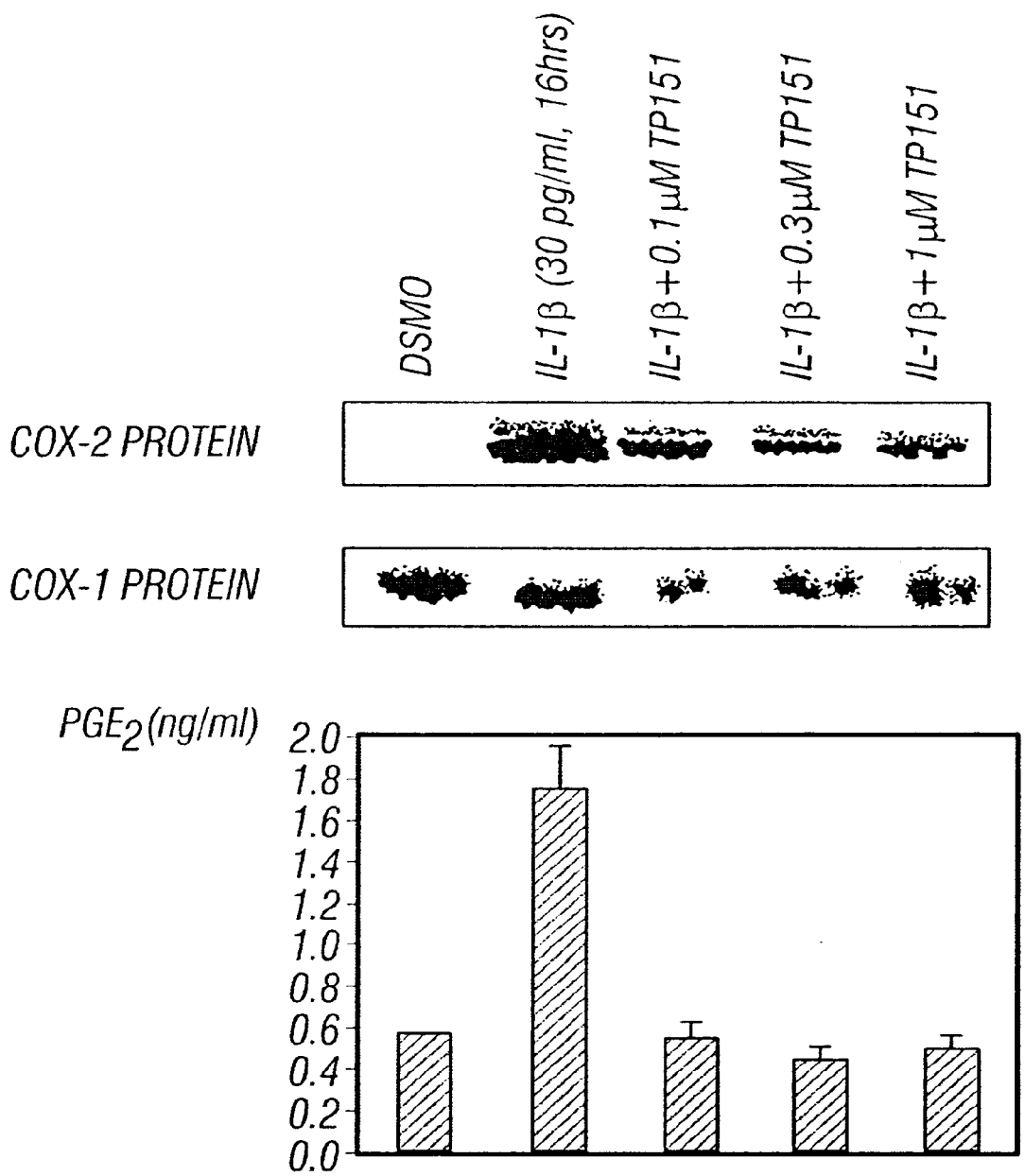
FIG. 1 illustrates the efficacy of a composition of the invention, 2-cyano-3,12-dioxoolean-1,9-dien-28oic acid (CDDO) (denoted "TP-151"), in supressing interleukin-1β (IL-1β)-induced COX-2 expression and prostaglandin $E_2$ ($PGE_2$) in human colon myofibroblast $^{18}Co$ cells.
Figure 2:
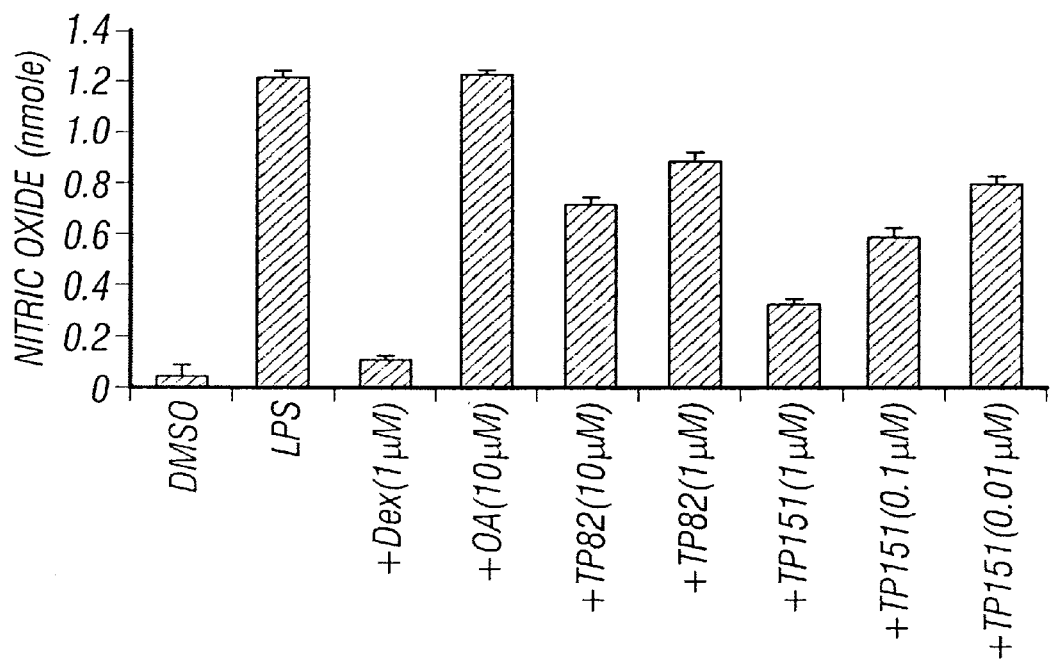
FIG. 2 is a comparison of the efficacy of various compounds on NO production induced by lipopolysaccharide (LPS) in rat microglia cells (brain macrophage cells), showing activity of TP151 favorable to that of dexamethasone, a glucocorticoid, thus indicating how a composition of the invention may be used to prevent or treat a neurodegenerative disease. "TP-82" refers to 3,11-dioxoolean-1,9-dien-28oic acid.
Figure 3:
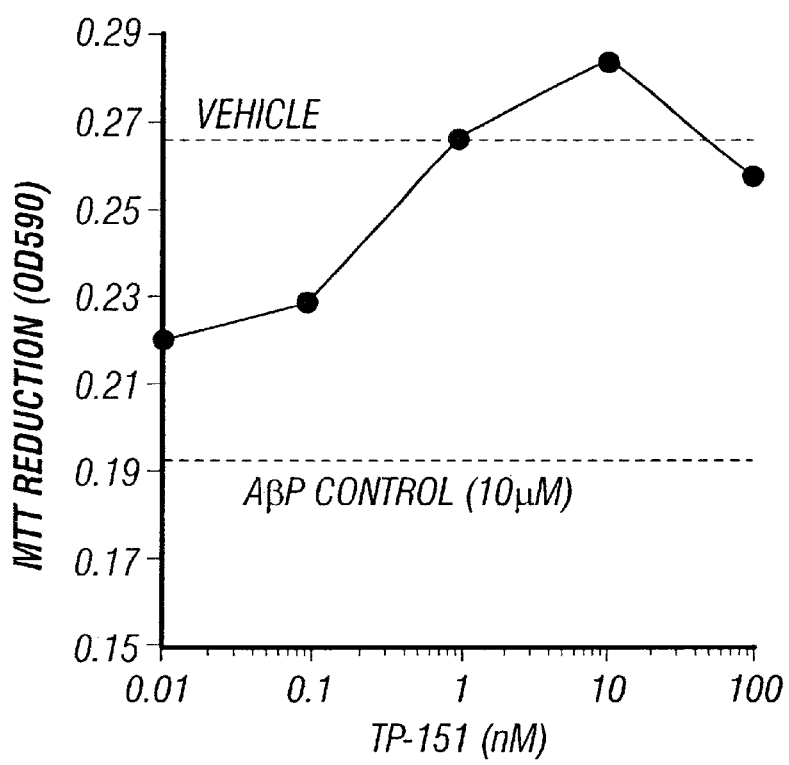
FIG. 3 illustrates the efficacy of TP151 in protecting in rat hippocampal neurons against toxicity induced by β-amyloid peptide, which is implicated in Alzheimer's disease.
Figure 4:
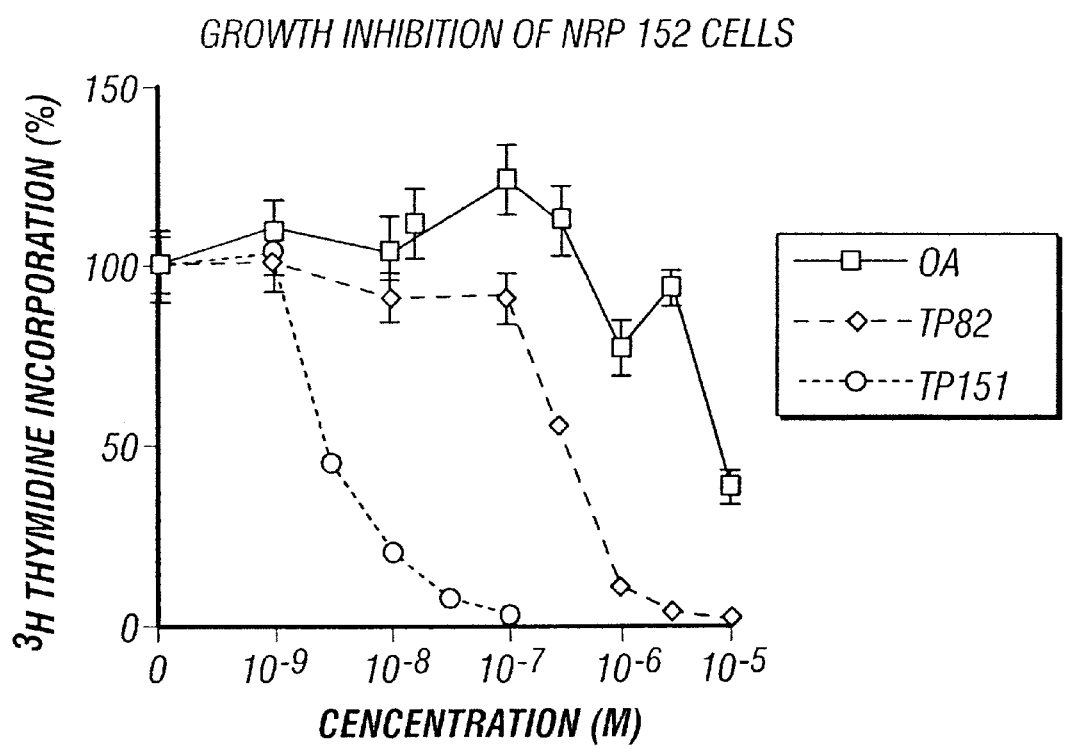
FIG. 4 illustrates, relevant to prevention or treatment or prostate cancer, the efficacy of TP151 in inhibiting growth of normal rat prostate cells (NRP152)
Figure 5:
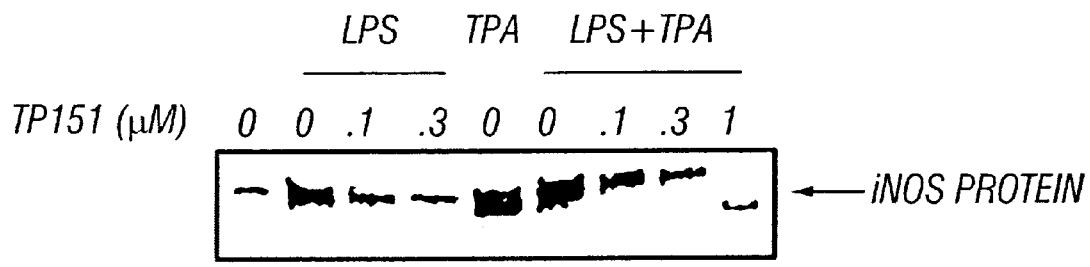
FIG. 5 illustrates the efficacy of TP 151 in modulating expression of iNOS protein in normal rat prostate cells (NRP152)
Figure 6:
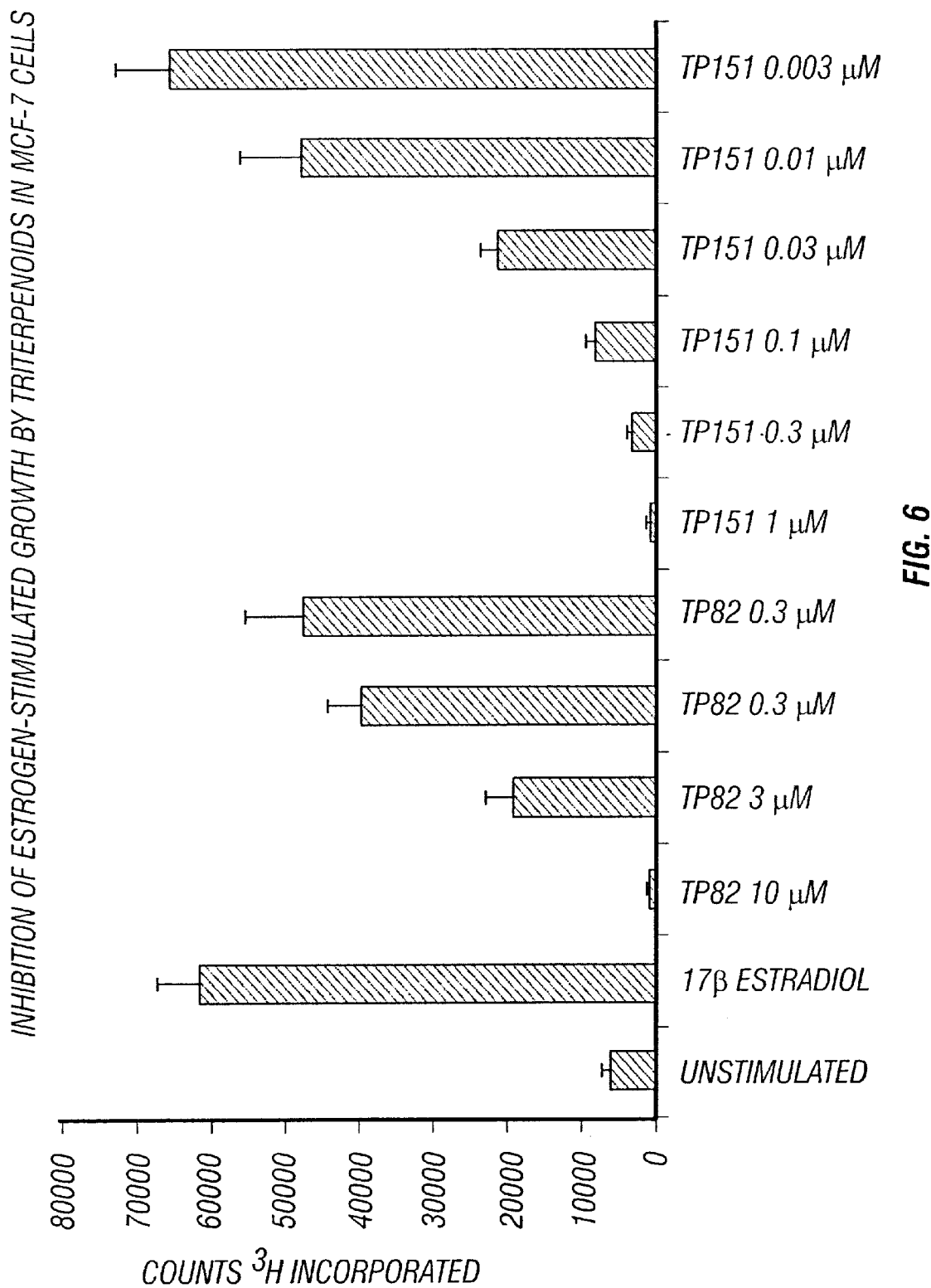
FIG. 6 illustrates, relevant to prevention or treatment or breast cancer, a comparison of the efficacy of various compounds including TP151 in inhibiting estrogen-stimulated growth in MCF-7 cells (breast cancer cell line)
Figure 7:
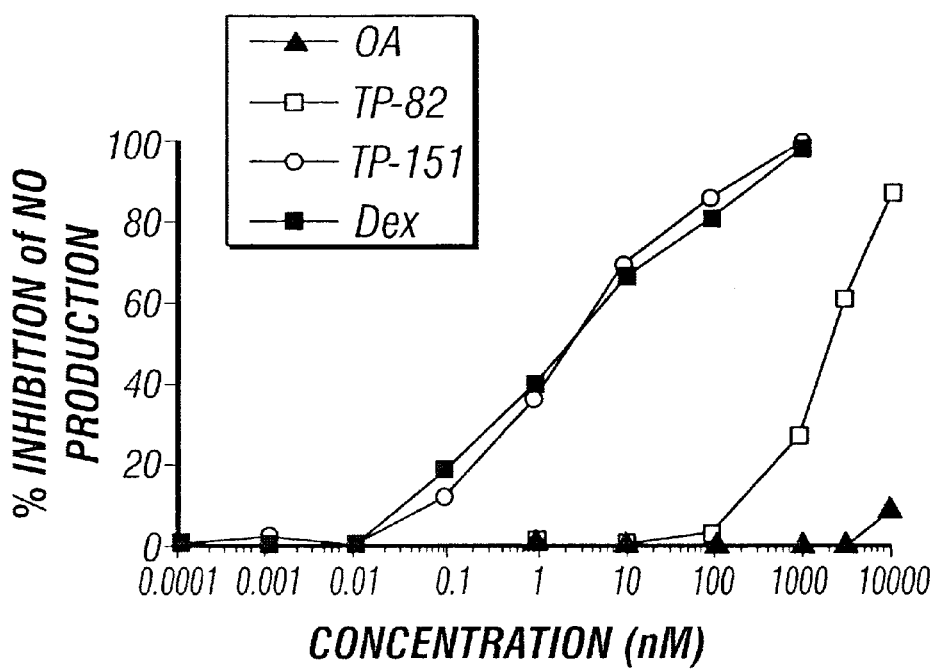
FIG. 7 illustrates, relevant to prevention or treatment of conditions with an inflammatory component, a comparison of the efficacy of various compounds on inhibiting NO production induced by LPS and IFN-γ in primary mouse macrophages, showing activity of TP151 favorable to that of dexamethasone.
Figure 8:
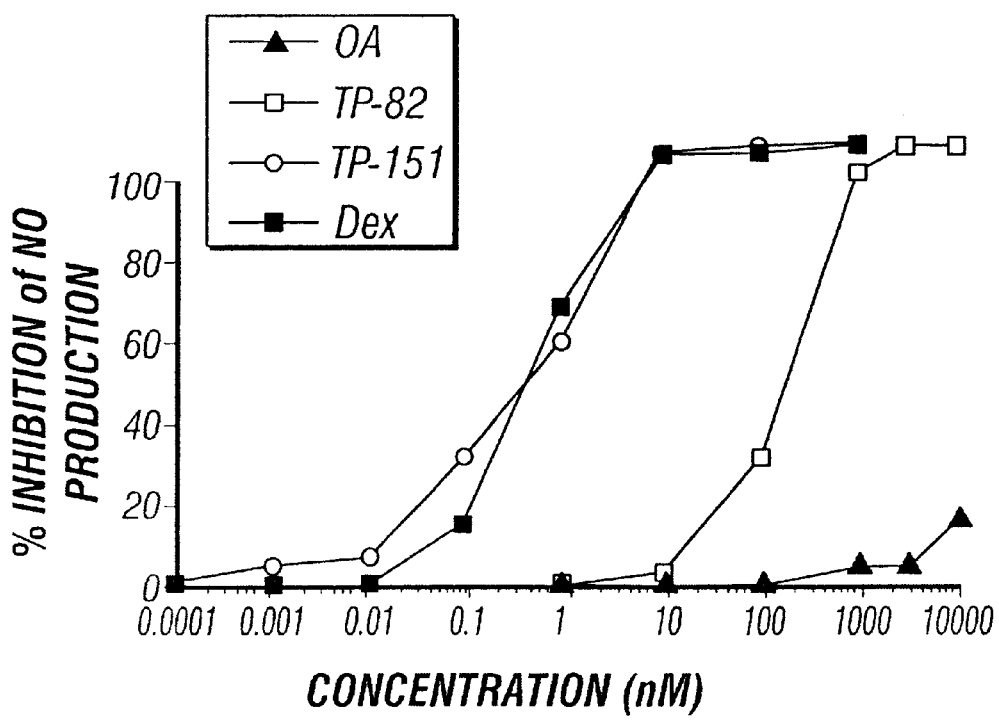
FIG. 8 is a comparison of the efficacy of various compounds on inhibiting NO production induced by IFN-γ in primary mouse macrophages.
Figure 9:
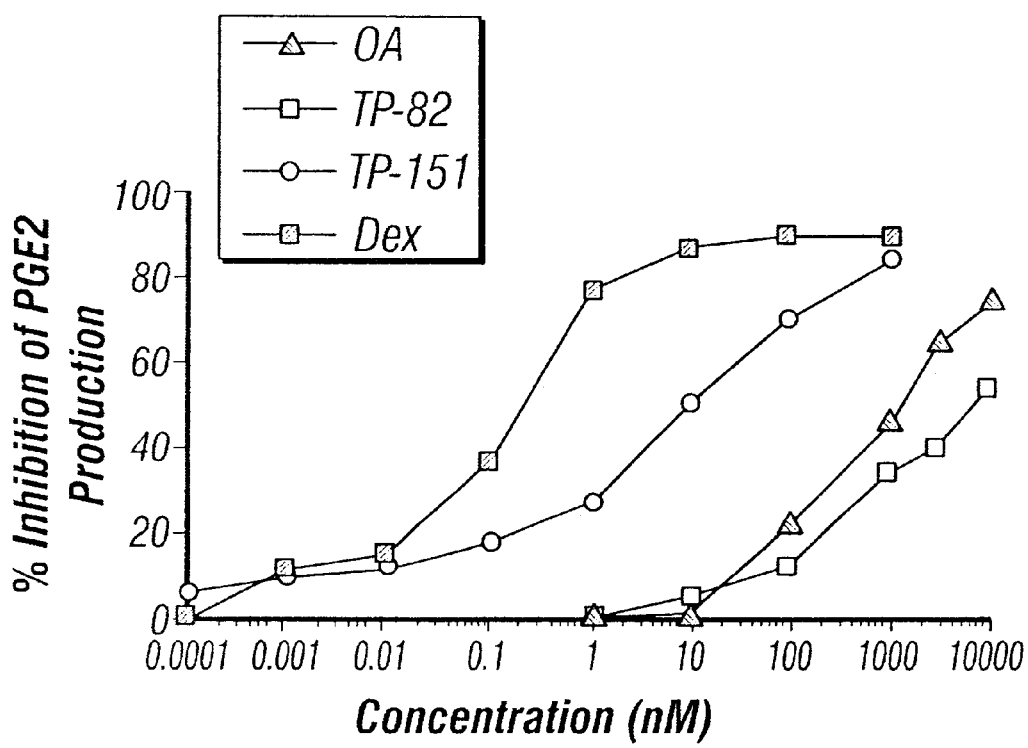
FIG. 9 illustrates a comparison of the efficacy of various compounds on inhibiting $PGE_2$ production induced by LPS and IFN-γ in primary mouse macrophages.
Figure 10:
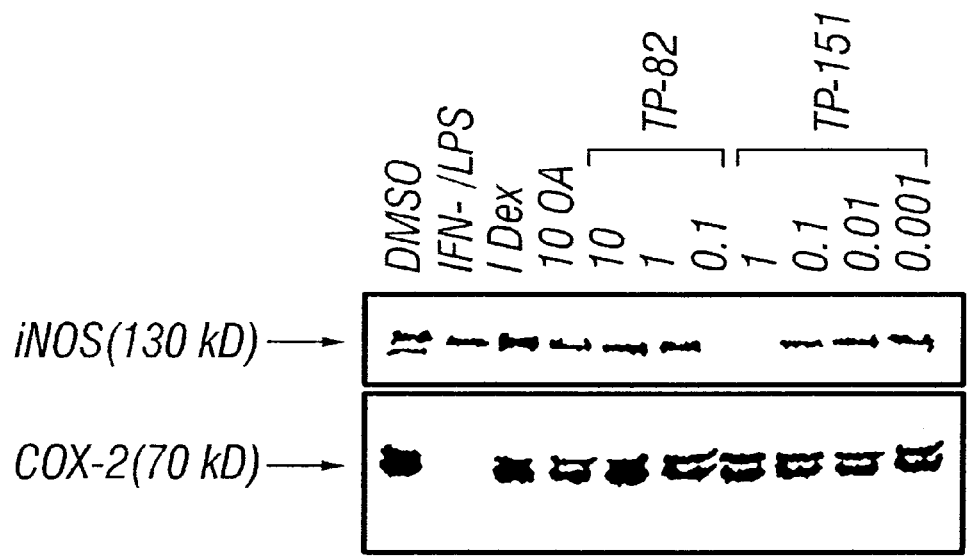
FIG. 10 illustrates a comparison of the efficacy of various compounds on supressing IFNγ and LPS-induced iNOS and COX-2 expression in primary mouse macrophages.

Before further description of the invention, certain terms employed in the specification, examples and appended claims are, for convenience, collected here.

Definitions

As used herein, the term "organic moiety" is intended to include carbon based functional groups such as alkyl, alkylamino, alkoxy, aryl, aralkyl, aryloxy, alkylthio, and alkylcarboxyl.

As used herein, the term "inorganic moiety" is intended to include non carbon-based groups or elements such as hydrogen, halo, amino, nitro, thiol, and hydroxyl.

As used herein, the term "electron withdrawing moiety" is known in the art, and refers to a group which has a greater electron-withdrawing than hydrogen. A variety of electron-withdrawing groups are known, and include halogens (e.g., fluoro, chloro, bromo, and iodo groups), nitro, cyano, $-NR_3^+$, $-SR_2^+$, $-NH_3^+$, $-SO_2R$, $-SO_2Ar$, $-COOH$, $-OAr$, $-COOR$, $-OR$, $-COR$, $-SH$, $-SR$, $-OH$, $-Ar$, and $-CH=CR_2$, where Ar is aryl, and R represents any appropriate organic or inorganic moiety and, preferably, alkyl moiety.

As used herein, the term "halosubstituted alkyl moieties" is intended to include alkyl moieties which have halogen moieties in the place of at least one hydrogen.

As used herein, the term "amino" means $-NH_2$; the term "nitro" means $-NO_2$; the term "halogen" designates $-F$, $-Cl$, $-Br$ or $-I$; the term "thiol" means SH; and the term "hydroxyl" means $-OH$. Thus, the term "alkylamino" as used herein means an alkyl group, as defined above, having an amino group attached thereto. The term "alkylthio" refers to an alkyl group, as defined above, having a sulfhydryl group attached thereto. The term "alkylcarboxyl" as used herein means an alkyl group, as defined above, having a carboxyl group attached thereto.

The term "aromatic group" is intended to include unsaturated cyclic hydrocarbons containing one or more rings. Aromatic groups include 5- and 6-membered single-ring groups which may include from zero to four heteroatoms, for example, benzene, pyrrole, furan, thiophene, imidazole, oxazole, thiazole, triazole, pyrazole, pyridine, pyrazine, pyridazine and pyrimidine, and the like. The aromatic ring may be substituted at one or more ring positions with, for example, a halogen, a lower alkyl, a lower alkenyl, a lower alkoxy, a lower alkylthio, a lower alkylamino, a lower alkylcarboxyl, a nitro, a hydroxyl, —CF$_3$, —CN, or the like.

The term "alkyl" refers to the saturated aliphatic groups, including straight-chain alkyl groups, branched-chain alkyl groups, cycloalkyl (alicyclic) groups, alkyl substituted cycloalkyl groups, and cycloalkyl substituted alkyl groups.

Moreover, the term "alkyl" (including "lower alkyl") as used throughout the specification and claims is intended to include both "unsubstituted alkyls" and "substituted alkyls", the latter of which refers to alkyl moieties having moieties replacing a hydrogen on one or more carbons of the hydrocarbon backbone. Such moieties can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylanino (including alkylcarbonylamino, arylcarbonylamino, carbamoyl and ureido), amidino, imino, sulfhydryl, alkylthio, arylthio, thiocarboxylate, sulfate, sulfonato, sulfamoyl, sulfonamido, nitro, trifluoromethyl, cyano, azido, heterocyclyl, aralkyl, or an aromatic or heteroaromatic moiety. It will be understood by those skilled in the art that the moieties substituted on the hydrocarbon chain can themselves be substituted, if appropriate. Cycloalkyls can be further substituted, e.g., with the moieties described above. An "aralkyl" moiety is an alkyl substituted with an aryl (e.g., phenylmethyl (benzyl)).

The term "alkoxy", as used herein, refers to a moiety having the structure —O-alkyl, in which the alkyl moiety is described above.

The term "aryl" as used herein includes 5- and 6-membered single-ring aromatic groups that may include from zero to four heteroatoms, for example, unsubstituted or substituted benzene, pyrrole, furan, thiophene, imidazole, oxazole, thiazole, triazole, pyrazole, pyridine, pyrazine, pyridazine and pyrimidine, and the like. Aryl groups also include polycyclic fused aromatic groups such as naphthyl, quinolyl, indolyl, and the like. The aromatic ring can be substituted at one or more ring positions with such moieties, e.g., as described above for alkyl groups. Preferred aryl groups include unsubstituted and substituted phenyl groups.

The term "aryloxy", as used herein, refers to a group having the structure —O-aryl, in which the aryl moiety is as defined above.

The term "amino," as used herein, refers to an unsubstituted or substituted moiety of the formula —NR$_a$R$_b$, in which R$_a$ and R$_b$ are each independently hydrogen, alkyl, aryl, or heterocyclyl, or R$_a$ and R$_b$, taken together with the nitrogen atom to which they are attached, form a cyclic moiety having from 3 to 8 atoms in the ring. Thus, the term "amino" is intended to include cyclic amino moieties such as piperidinyl or pyrrolidinyl groups, unless otherwise stated. An "amino-substituted amino group" refers to an amino group in which at least one of R$_a$ and R$_b$, is further substituted with an amino group.

As used herein, the term "subject" is intended to include living organisms in which certain conditions as described herein can occur. Examples include humans, monkeys, cows, sheep, goats, dogs, cats, mice, rats, and transgenic species thereof. In a preferred embodiment, the subject is a primate. In an even more preferred embodiment, the primate is a human. Other examples of subjects include experimental animals such as mice, rats, dogs, cats, goats, sheep, pigs, and cows. The experimental animal can be an animal model for a disorder, e.g., a transgenic mouse with an Alzheimer's-type neuropathology. A subject can be a human suffering from a neurodegenerative disease, such as Alzheimer's disease, or Parkinson's disease.

As used herein, the term "IC$_{50}$" refers to an inhibitory dose which is 50% of the maximum response obtained.

Other abbreviations used herein are as follows: CDDO, 2-cyano-3,12-dioxoolean-1,9-dien-28-oic acid; DMSO, dimethyl sulfoxide; iNOS, inducible nitric oxide synthase; COX-2, cyclooxygenase-2; NGF, nerve growth factor; IBMX, isobutylmethylxanthine; FBS, fetal bovine serum; GPDH, glycerol 3-phosphate dehydrogenase; RXR, retinoid X receptor; TGF-β, transforming growth factor-β; IFN-γ, interferon-γ; LPS, bacterial endotoxic lipopolysaccharide; TNF-α, tumor necrosis factor-α; IL-1β, interleukin-1β; GAPDH, glyceraldehyde-3-phosphate dehydrogenase; MTT, 3-[4,5-dimethylthiazol-2-yl]-2,5-diphenyltetrazolium bromide; TCA, trichloroacetic acid.

The compounds may be administered, e.g., orally or by subcutaneous, intravenous, intraperitoneal, etc. administration (e.g. by injection). Depending on the route of administration, the active compound may be coated in a material to protect the compound from the action of acids and other natural conditions which may inactivate the compound.

To administer the therapeutic compound by other than parenteral administration, it may be necessary to coat the compound with, or co-administer the compound with, a material to prevent its inactivation. For example, the therapeutic compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., (1984) *J. Neuroimmunol.* 7:27).

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a subject.

Active compounds are administered at a therapeutically effective dosage sufficient to treat a condition associated with a condition in a subject. A "therapeutically effective dosage" preferably reduces the amount of symptoms of the condition in the infected subject by at least about 20%, more preferably by at least about 40%, even more preferably by at least about 60%, and still more preferably by at least about 80% relative to untreated subjects. For example, the efficacy of a compound can be evaluated in an animal model system that may be predictive of efficacy in treating the disease in humans, such as the model systems shown in the Example and Figures.

The invention features a composition of matter having the formula:

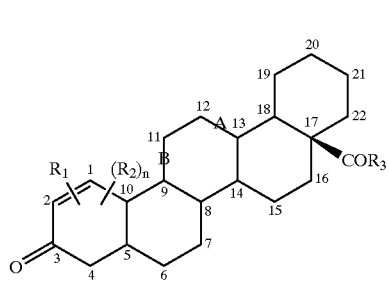

(I)

wherein A or B is a single or double bond and $C_{11}$ or $C_{12}$ have substituted thereon =X which is an organic or inorganic moiety; $R_1$ is an organic or inorganic moiety which may be substituted anywhere on the six-membered ring denoted by positions 1 through 10; $R_2$ and $R_3$ are hydrogen or organic or inorganic moieties, wherein an $R_2$ group may be substituted anywhere on the structure represented in the formula; and n is a number from 0 to 100.

The invention further features a composition of matter having the formula:

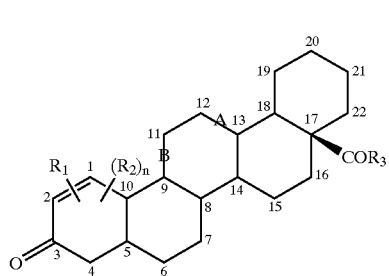

(I)

wherein either A or B is a double bond such that when A is a double bond, $C_{11}$ has substituted thereon =X which is an organic or inorganic moiety and when B is a double bond, $C_{12}$ has substituted thereon =X; $R_1$ is an organic or inorganic moiety which may be substituted anywhere on the six-membered ring denoted by positions 1 through 10; $R_2$ and $R_3$ are hydrogen or organic or inorganic moieties, wherein an $R_2$ group may be substituted anywhere on the structure represented in formula (I); and n is a number from 0 to 100).

$R_1$ may be an electron-withdrawing group, e.g., cyano, aryl, and halosubstituted alkyl moieties. Preferably, $R_1$ may include cyano, halo, or —OR', wherein R' is H or an organic moiety, e.g., acetyl or carboxyl group. $R_1$ may be substituted anywhere on the six-membered ring denoted by positions 1 through 10, but in a preferred embodiment $R_1$ is at position 2 and in a more preferred embodiment $R_1$ is a cyano group at position 2.

In a more preferred embodiment of formula (I), B is a double bond, X is O, $R_3$ is —OH, and $R_1$ is a cyano group, preferably at position 2. Examples of preferred compounds include 3,11-dioxoolean-1,12-dien-28oic acid, 2-cyano-3,11-dioxoolean-1,12-dien-28oic acid and 2-cyano-3,12-dioxoolean-1,9-dien-28oic acid.

In another aspect, the invention features a triterpenoid composition effective for modulating IFN-γ-induced NO production in macrophages, said composition having an $IC_{50}$ value of at least less than 0.6 µM, more preferably less than 0.001 µM.

In another aspect a method of preventing or treating a disorder characterized by overexpression of iNOS or COX-2 genes is presented, comprising administering to a subject a pharmaceutically effective amount of a composition of formula (I), such that the disorder is prevented or treated. In a preferred embodiment, the disorder includes cancer, neurodegenerative diseases, and rheumatoid arthritis. In a further preferred embodiment, the neurodegenerative disease includes Parkinson's disease, Alzheimer's disease, multiple sclerosis, and amyotrophic lateral sclerosis. The cancer may include breast cancer, prostate cancer, colon cancer, brain cancer, and bone cancer.

In another aspect, the invention features a method of modulating excessive nitric oxide or prostaglandin formation in a subject, comprising administering to a subject a pharmaceutically effective amount of a composition of formula (I), such that the nitric oxide or prostaglandin formation is modulated.

In another aspect, the invention features a method of modulating transcription or translation of iNOS or COX-2 genes in a subject comprises administering to a subject a pharmaceutically effective amount of a composition of formula (I), such that the transcription or translation of iNOS or COX-2 genes is modulated.

In another aspect, the invention features a method of preventing or treating a neurodegenerative disease, comprising administering to a subject a pharmaceutically effective amount of a composition of formula (I), such that the neurodegenerative disease is prevented or treated. In a preferred embodiment, the neurodegenerative disease includes Parkinson's disease, Alzheimer's disease, multiple sclerosis, and amyotrophic lateral sclerosis.

The compounds of the present invention are compounds based on the five ring structure shown in formula (I), which, in a preferred embodiment, are based on a triterpenoid structure as shown below:

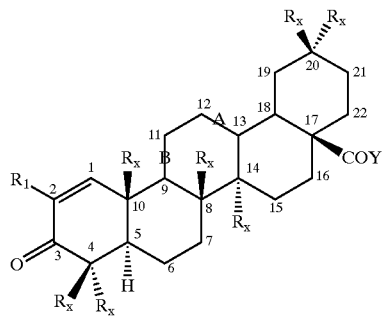

wherein $R_x$ represents any organic or inorganic moiety, preferably methyl; and Y is preferably hydroxyl. Triterpenoids, like the steroids, are formed in nature by the cyclization of squalene, with the retention of all 30 carbon atoms in molecules such as ursolic acid (UA) and oleanoic acid (OA). Although OA and UA are known to have numerous pharmacological activities, the potency of these naturally occurring molecules is relatively weak. The derivatives of OA and UA as disclosed herein, however, are more potent than OA and UA.

In a preferred embodiment, such compounds include derivatives of ursolic acid and oleanoic acid. In a particularly preferred embodiment, derivatives of OA, e.g., 2-cyano-3,12-dioxoolean-1,9-dien-28oic acid (CDDO):

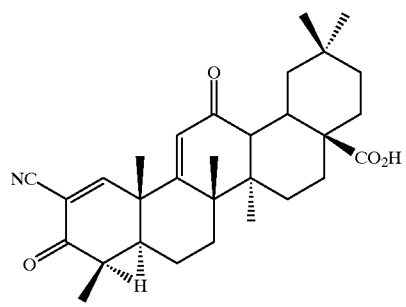

have been found to be effective in suppression of human breast cancer cell growth, and highly potent in many vitro assay systems such as: suppression of nitric oxide and prostaglandin production in macrophages, inhibition of growth of human breast cancer cells, suppression of nitric oxide formation in rat prostate cells, and suppression of prostaglandin formation in human colon fibroblasts, as detailed in the Figures.

These compounds have utility for prevention and treatment of cancer, Alzheimer's disease, Parkinson's disease, multiple sclerosis, amyotrophicleteral sclerosis, rheumatoid arthritis, inflammatory bowel disease, and all other diseases whose pathogenesis is believed to involve excessive production of either nitric oxide or prostaglandins.

The aberrant or excessive expression of either iNOS or COX-2 has been implicated in the pathogenesis of many disease processes, including carcinogenesis in the colon. Thus, overexpression of the gene for COX-2 is an early and central event in colon carcinogenesis (Prescott and White, 1996; Dubois et al., 1996). Mice with defects in the APC (adenomatous polyposis coli) gene develop large numbers of intestinal polyps at an early age, and marked elevations in COX-2 enzyme levels have been found in these polyps. These animal findings correlate with the finding of elevated levels of COX-2 mRNA and protein in many human primary colon cancers and colon cancer cell lines (Prescott and White, 1996), and it is believed that this elevation in COX-2 leads to a suppression of apoptosis, which would ordinarily lead to death of preneoplastic cells (Tsujii and DuBois, 1996). The functional relevance of COX-2 to intestinal tumorigenesis has been demonstrated by knockout of the COX-2 gene and the subsequent mating of mice bearing this knockout with polyp-forming mice bearing lesions in the APC gene; the COX-2 knockout caused a dramatic diminution in the number of polyps in the offspring (Oshima et al., 1996). Furthermore, treatment of experimental animals with either selective COX-2 inhibitors or non-selective COX-1/COX-2 inhibitors has been reported to be a potent approach to chemoprevention of intestinal cancer (Marnett, 1992; Oshima et al., 1996; Boolbol et al., 1996; Reddy et al., 1996; Sheng et al., 1997). As for the role of iNOS in carcinogenesis, it is clear that NO is a potent mutagen (Tamir and Tannebaum, 1996), and that nitric oxide can also activate COX-2 (Salvemini et al., 1993, 1994). Furthermore, there is a marked increase in iNOS in rate colon tumors induced by the carcinogen, azoxymethane (Takahashi et al., 1997).

MS is known to be an inflammatory condition of the central nervous system (Williams, Ulvestad and Hickey, 1994; Merrill and Beneviste, 1996; Genain and Nauser, 1997). Inflammatory, oxidative, or immune mechanisms may be involved in the pathogenesis of MS, AD, PD, and ALS (Bagasra et al., 1995; Griffin et al., 1995; McGeer and McGeer, 1995; Good et al., 1996; Simonian and Coyle, 1996; Kaltschmidt et al., 1997). Both reactive astrocytes and activated microglia have been implicated in causation of NDD/NID; there has been a particular emphasis on microglia as cells that synthesize both NO and prostaglandins as products of the respective enzymes, iNOS and COX-2. De novo formation of these enzymes may be driven by inflammatory cytokines such as interferon-gamma or interleukin-1. In turn, excessive production of NO may lead to inflammatory cascades and/or oxidative damage in cells and tissues of many organs, including neurons and oligodendrocytes of the nervous system, with consequent manifestations in AD and MS, and possible PD and ALS (Coyle and Puttfarcken, 1993; Goodwin et al., 1995; Beal, 1996; Good et al., 1996; Merrill and Benvenist, 1996; Simonian and Coyle, 1996; Vodovotz et al., 1996). Epidemiologic data indicate that chronic use of NSAID's which block synthesis of prostaglandins from arachidonate, markedly lower the risk for development of AD (McGeer et al., 1996; Stewart et al., 1997). Thus, agents that block formation of NO and prostaglandins, may be used in approaches to prevention and treatment of NDD.

Further disclosed herein are the synthesis and biological activities of a new synthetic oleanane triterpenoid, CDDO, that has three important properties: 1) it is a potent agent for induction of differentiation in both malignant and non-malignant cells; 2) it is active at nanomolar levels as an inhibitor of proliferation of many malignant or premalignant cells; and 3) it is 100- to 500-fold more potent than any previous triterpenoid in suppressing the de novo synthesis of the inflammatory enzymes, iNOS and COX-2. These three actions are important for the development of a useful new chemopreventive agent, and they are also relevant to therapy of malignancy itself as well.

The practice of the present invention will employ, unless otherwise indicated, conventional techniques of cell biology, cell culture, molecular biology, microbiology, recombinant DNA, and immunology, which are within the skill of the art. Such techniques are explained fully in the literature. See, for example, *Genetics; Molecular Cloning A Laboratory Manual*, 2nd Ed., ed. by Sambrook, J. et al. (Cold Spring Harbor Laboratory Press (1989)); *Short Protocols in Molecular Biology*, 3rd Ed., ed. by Ausubel, F. et al. (Wiley, N.Y. (1995)); *DNA Cloning*, Volumes I and II (D. N. Glover ed., 1985); *Oligonucleotide Synthesis (M. J. Gait ed. (1984))*; Mullis et al. U.S. Pat. No: 4,683,195; *Nucleic Acid Hybridization* (B. D. Hames & S. J. Higgins eds. (1984)); the treatise, *Methods In Enzymology* (Academic Press, Inc., N.Y.); *Immunochemical Methods In Cell And Molecular Biology* (Mayer and Walker, eds., Academic Press, London (1987)); *Handbook Of Experimental Immunology*, Volumes I–IV (D. M. Weir and C. C. Blackwell, eds. (1986)); and Miller, *J. Experiments in Molecular Genetics* (Cold Spring Harbor Press, Cold Spring Harbor, N.Y. (1972)).

The invention is further illustrated by the following examples which should not be construed as further limiting the subject invention. The contents of all references, issued patents, and published patent applications cited throughout this application including the background are hereby incorporated by reference. A demonstration of efficacy of the therapeutic compounds of the present invention in the model(s) described in the Examples and Figures is predictive of efficacy in humans.

EXAMPLE 1

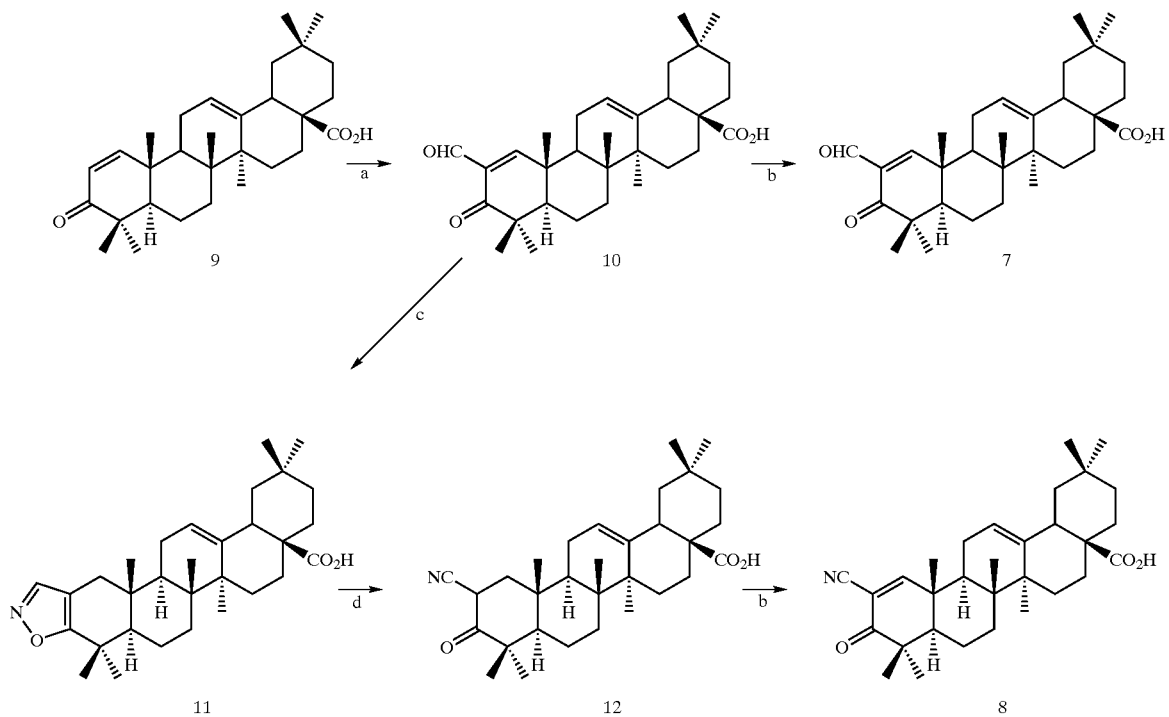

Scheme I

Scheme 2

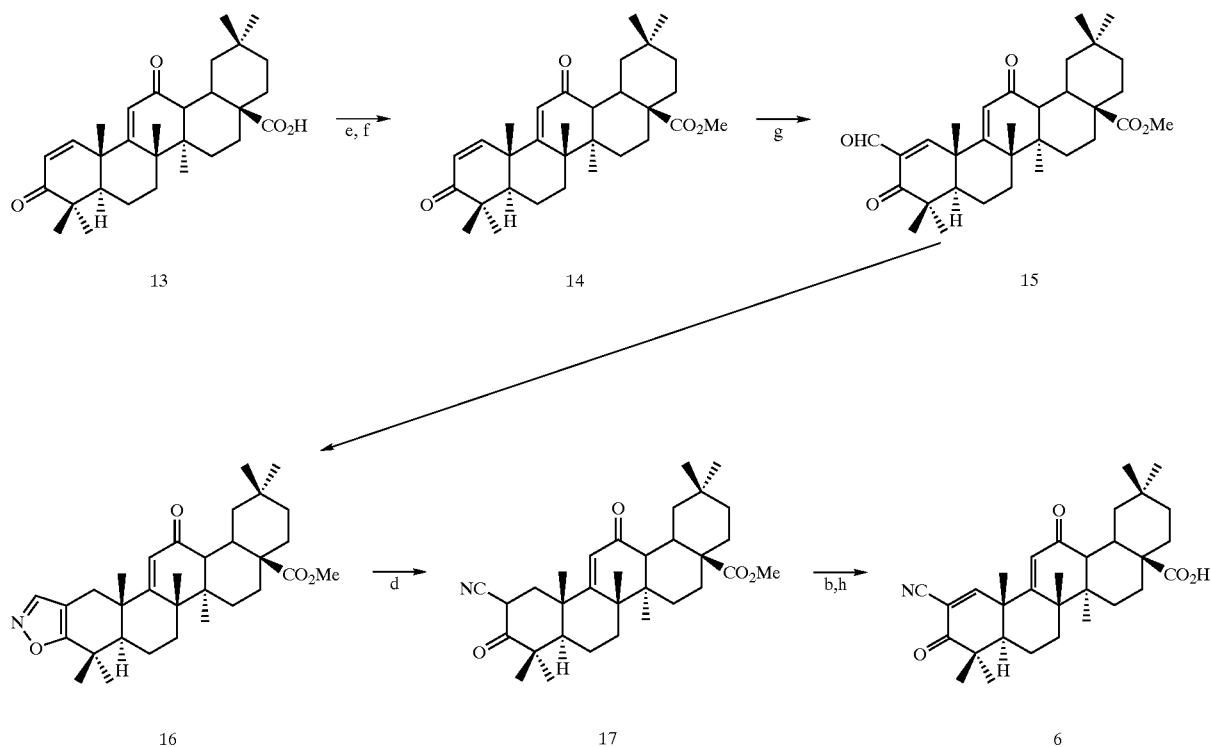

a: HCO₂Et/MeONa/THF, b: PhSeCl/AcOEt; 30% H₂O₂/THF, c: NH₂OH—HCl/EtOH/H₂O, d: MeONa/MeOH/Et₂O, e: KOH/MeOH, f: Jones, g: HCO₂Et/MeONa/PhH, h: LiI/DMF Compound 10 was prepared by formylation of OA (Compound 9) (Simonsen and Ross, 1957) with ethyl formate in the presence of sodium methoxide in THF (Clinton et al., 1961). Compound 7 was obtained by introduction of a double bond at C-1 of Compound 10 with phenylselenenyl chloride in ethyl acetate and sequential addition of 30% hydrogen peroxide (Sharpless et al., 1973). Compound 11 was synthesized from Compound 10 by addition of hydroxylamine in aqueous ethanol; cleavage of Compound 11 with sodium methoxide gave Compound 12 (Johnson and Shelberg, 1945). Compound 14 was prepared from Compound 13 (Picard et al, 1939) by alkali hydrolysis followed by Jones oxidation. Compound 15 was prepared by formylation of Compound 14 with ethyl formate in the presence of sodium methoxide in benzene. Compound 16 was synthesized from Compound 15 by addition of hydroxylamine. Cleavage of 16 with sodium methoxide gave Compound 17. Compound 6 (CDDO) was prepared by introduction of a double bond at C-1 of Compound 17 with phenylselenenyl chloride in ethyl acetate and sequential addition of 30% hydrogen peroxide, followed by halogenolysis with lithium iodide in DMF (Dean, P. D. G., 1965).

The inhibitory activities of these compounds and dexamethasone on IFN-γ induced NO production in mouse macrophages is shown below in Table 1. The following procedure for the assay ws used. Macrophages were harvested from female mice injected intraperitoneally four days previously with 4% thioglycollate. These cells were seeded in 96-well tissue culture plates and incubated with 4 ng/mL IFN-γ in the presence or absence of inhibitory test compounds. After 48 hours NO production (measured as nitrite by the Griess reaction) was determined. Full details of the assay are given in Ding et al., 1990; Bogdan et al, 1992. Compound 6 (CDDO) showed excellent inhibitory activity ($IC_{50}$, 1 nM) similar to that of dexamethasone.

TABLE 1

$IC_{50}$ $(\mu M)^a$ Values for Inhibition of IFN-γ-Induced NO Production in Mouse Macrophages.

| Compound | $IC_{50}$ ($\mu M$) | Compound | $IC_{50}$ ($\mu M$) |
|---|---|---|---|
| dexamethasone | 0.001 | 5 | 27 |
| 1 | 0.6 | 6 | 0.001 |
| 2 | 0.9 | 7 | >1.0[b] |
| 3 | 6 | 8 | .9 |
| 4 | 30 | | |

[a]$IC_{50}$ ($\mu M$) values of compounds 1–5, 7 and 8 were determined in the range of 0.01–40 $\mu M$ (4-fold dilutions) and the ones of dexamethasone and 6 were determined in the range of 1 $\mu M$–0.1 pM (10 fold dilutions). Values are the average of two separate experiments.
[b]Compound 7 was very toxic above 1 $\mu M$ and not active below 1 $\mu M$.

All new compounds 6–8 exhibited satisfactory spectral data including high-resolution mass spectra and elemental analysis.

For the following examples, stock solutions of CDDO (0.01 M) were made in DMSO and aliquots frozen at −20° C. Serial dilutions were made in DMSO before addition to cell culture media. Primary rat microglia and hippocampal neurons were isolated and cultured as described by Flaris et al., 1993 and Ren and Flanders, 1996.

Figure 11A:
FIGS. 11(A)–(H) shows induction of differentiation by CDDO in LCDB leukemia cells (A–D), PC12 cells (E–H)
Figure 11B:
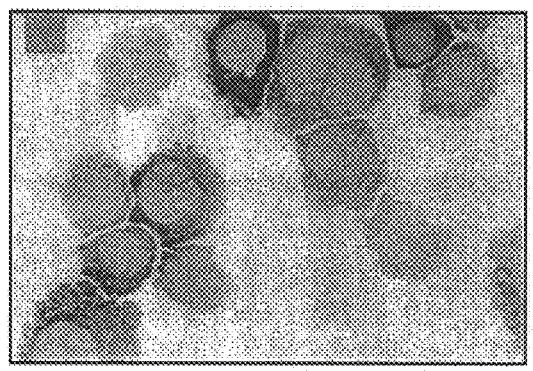
Figure 11C:
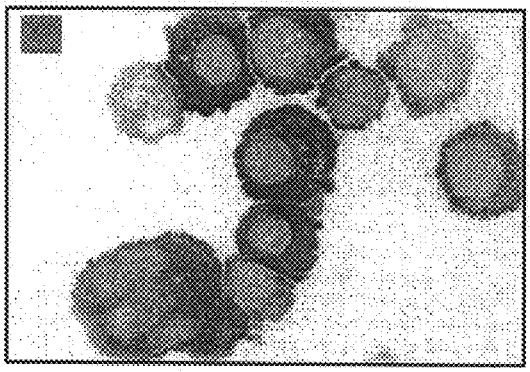
Figure 11D:
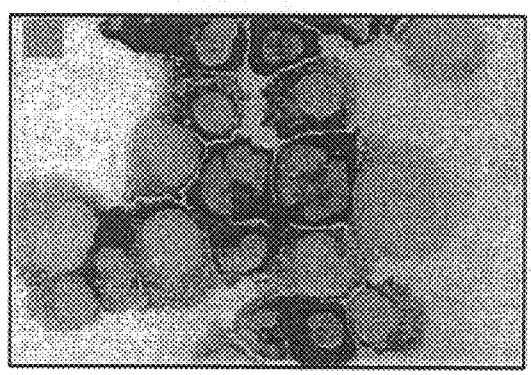
Figure 11E:
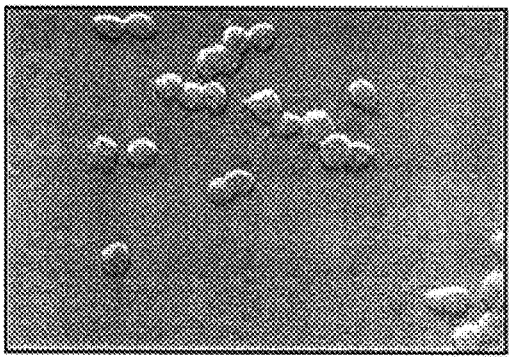
Figure 11F:
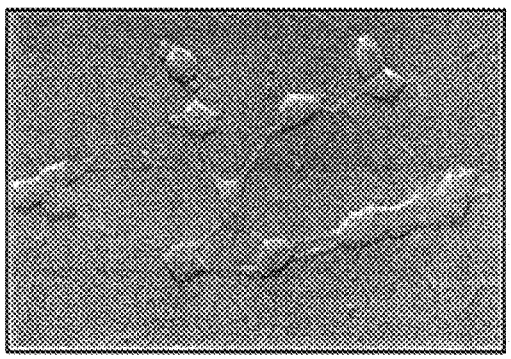
Figure 11G:
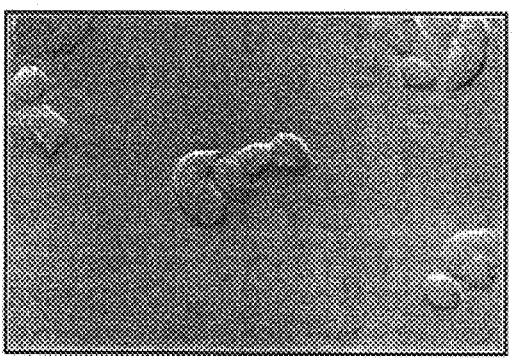
Figure 11H:
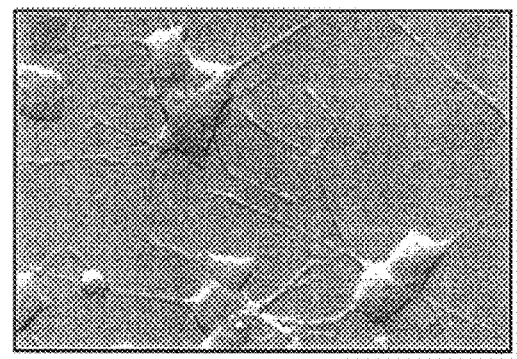
Figure 12A:
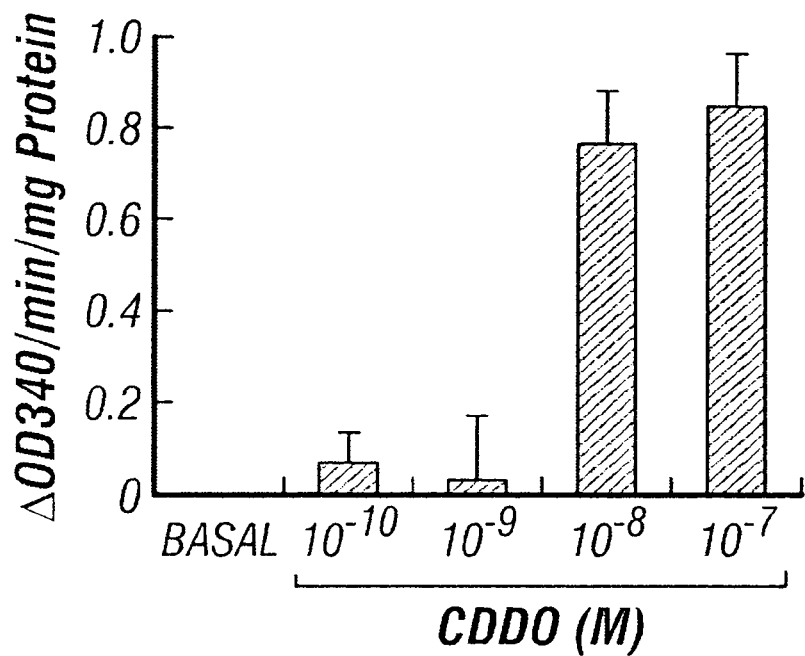
FIGS. 12(A)–(B) shows induction of differentiation by CDDO in 3T3-L1 fibroblasts.
Figure 12B:
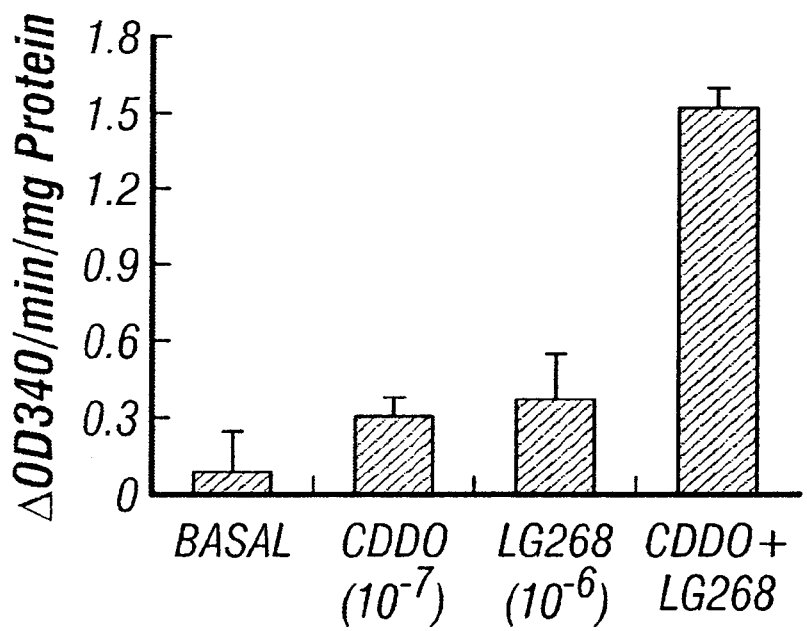

EXAMPLE 2
Induction of Differentiation in Myclogenous Leukemia Cells, PC12 Pheochromocytoma Cells, and 3T3-L1 Fibroblasts CDDO induces monocytic differentiation in the poorly differentiated LCDB acute myelogenous leukemia cell line, derived from a chemotherapy-resistant patient at the NCI Pediatric Oncology Branch. FIG. 11 illustrates LCDB cells seeded in RPMI 1640/2% FBS, either alone (11A), with 2.5 ng/ml TGF-β1 (11B), with $10^{-8}$ M CDDO (11C), or with both TGF-β1 and CDDO (11D). After 48 h, cytospin slide preparations were made and stained for α-naphthyl acetate esterase activity (kit from Sigma). PC12 cells were cultured for 5 days in gridded dishes in DMEM/10% FBS and 5% horse serum (Smith et al., 1997), either alone (11E), with 100 ng/ml 7S NGF (11F), with $10^{-6}$ M CDDO (11G), or with both NGF and CDDO (11H). Cells were plated in triplicate, and for each treatment similar results were observed in at least two separate platings of cells. Methods for quantitative image analysis of size of cells and neurites have been described (De la Torre et al., 1997). Control cells in FIG. 11E are approximately 10 μm in diameter. 3T3-L1 cells were grown to confluency in DMEM/5% calf serum, and then treated once with CDDO in DMEM/10% FBS (FIG. 12A) or with CDDO and/or LG100268 in DMEM/10% FBS (FIG. 12B). Every two days thereafter, medium was changed to DMEM/10% FBS, without added CDDO or LGO100268. Cells were harvested on day 8 (FIG. 12A) or day 6 (FIG. 12B), and GPDH was measured in lysates, using a standard assay for consumption of NADH at 340 nm (Wise and Green, 1979). These cells do not express the monocyte/macrophage marker, α-naphthyl esterase (FIG. 11A). However, within 48 h, CDDO ($10^{-8}$ M) induced the activity of this enzyme, as determined histochemically (FIG. 11C). Treatment of LCDB cells with TGF-β1 (2.5 ng/ml) also induced α-naphthyl esterase activity (FIG. 11B), and there was an additive effect when both agents are used (FIG. 11D). It has been shown that CDDO has differentiative effects, either by itself or in combination with TGF-β1, on the human monocytic leukemia line, THP-1, and the human promyelocytic leukemia line, NB4 (data not shown).

The rat pheochromocytoma cell line, PC12, has been widely used to study neuronal development and differentiation. Treatment of these tumor cells with NGF is known to induce a neuronal phenotype, with extensive neurite outgrowth (Greene and Rischler, 1976; Guroff 1985). CDDO markedly potentiates these effects of NGF. FIGS. 11E and F show the induction of neurite outgrowth by NGF (100 ng/ml). Although CDDO ($10^{-6}$M) by itself does not induce neurite formation, it does cause the cells to adopt a larger, flatter morphology (FIG. 11G). When used in combination with NGF, CDDO (FIG. 11H) almost doubled the number of primary neurites/cell (from 1.2±0.2 S.E.M. to 2.1±0.1, p<0.001), and caused a greater than 3-fold increase in length of neurites (from 28±6 to 99±9 microns, p<0.001), and a 5-fold increase in neurite branching/cell (from 0.23±0.06 to 1.13±0.08, p<0.001). Thus, CDDO enhances neuronal differentiation of PC12 cells by increasing cell size, as well as the extent and complexity of neurite arborization.

A third cell type in which CDDO induces differentiation is the 3T3-L1 fibroblast. These non-neoplastic fibroblasts are classically induced to form adipocytes by the combination of insulin, dexamethasone, and IBMX (Green and Kehinde, 1974; Bernlohr et al., 1984). Treatment with CDDO (FIG. 12A) at doses as low as $10^{-8}$ M (in the absence of added insulin, dexamethasone, and IBMX) caused adipogenic differentiation, as measured by induction of the marker, GPDH (Wise and Green, 1979), known to be a key enzyme in triglyceride synthesis. The results with the enzyme assay have been confirmed by oil red O staining for fat droplets (data not shown). Furthermore, CDDO acts synergistically with the RXR-selective retinoid, LG100268 (Boehm et al., 1995) to promote adipogenic differentiation (FIG. 12B).

EXAMPLE 3

CDDO Inhibits Proliferation of Many Malignant or Premalignant Cells

Figure 13A:
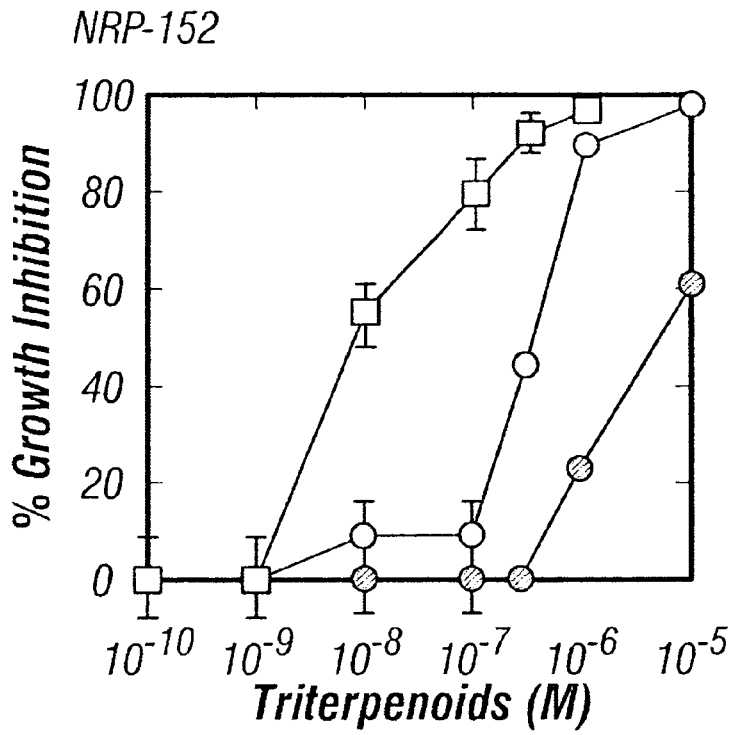
FIGS. 13(A)–(B) illustrate dose-response curves for suppression of cell growth in NRP-152 and MCF-7 cells by CDDO (■), TP-82 (○), and oleanolic acid (●).
Figure 13B:
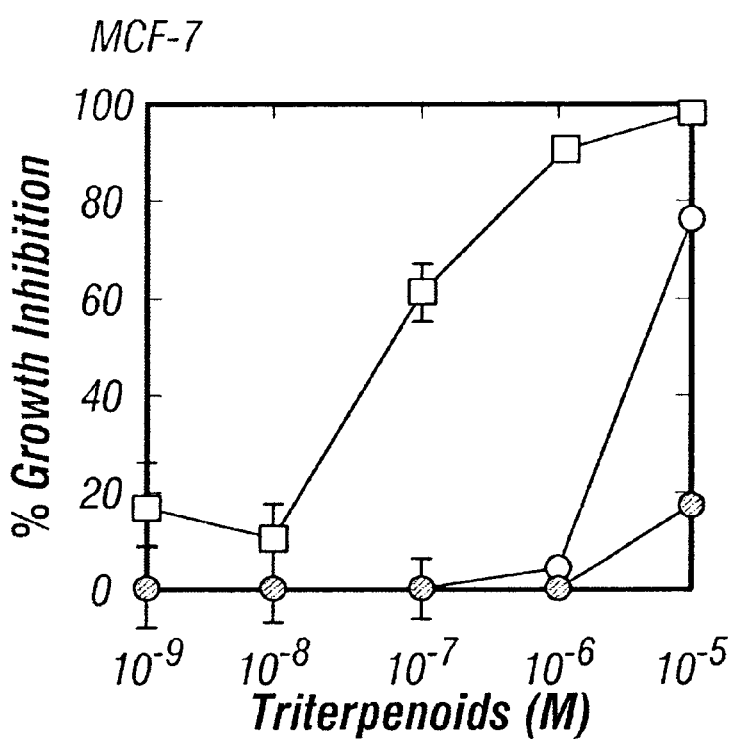

Inhibitors of cell proliferation are known to be useful chemopreventive and chemotherapeutic agents. CDDO was tested against a wide variety of cells derived from highly aggressive leukemias and carcinomas, as well as from non-neoplastic tissues. NRP-152 cells were grown as described in Danielpour et al., 1994. MCF-7 cells were grown in phenol red-free RPMI 1640/10% charcoal-stripped FBS with added 17-β-estradiol (10 pM). Triterpenoids were added at the time of plating, and 72 h later $^3$H-thynidine (1 μCi/well) was added for the final 2 h of incubation. Incorporation of thymidine was measured after cells were precipitated with TCA (10%), washed, and solubilized. The symbols used in FIGS. 13(A)–(B) ale CDDO, |; TP-82, ○; and oleanolic acid, ●.

Typical dose-response curves are shown in FIGS. 13 (A)–(B) for two cell types, human MCF-7 breast carcinoma and rat NRP-152 non-malignant prostate epitheliumn (Danielpour et al., 1994). CDDO is highly active in the nanomolar range in suppressing thymidine incorporation in these cells, while TP-82 is markedly less active, and oleanolic acid, is virtually without activity at concentrations of 1 μM or less.

Results obtained with other cancer cells are shown in Table 2. Note that: (1) several lines of estrogen receptor-negative breast cancer cells are sensitive to CDDO, as well as estrogen receptor-positive MCF-7 cells; (2) even if tumor cells have a Smad-4/DPC4 mutation and are therefore insensitive to the growth-inhibitory actions of TGF-β (Schutte et al., 1996; Zhou et al., 1998; Heldin et al., 1997), they still may respond to CDDO, as can be seen in the case of SW626 ovarian carcinoma, CAPAN-1 and AsPc-1 pancreatic carcinoma, and MDA-MB-468 breast carcinoma cells; (3) many leukemia cells, especially of the myeloid lineage, are highly sensitive to CDDO.

TABLE 2

Inhibition of cell proliferation by CDDO

| Cell | Cell type | $IC_{50}$ (M) |
|---|---|---|
| MCF-7 | ER positive breast carcinoma | $3 \times 10^{-8}$ |
| MDA-MB-231 | ER negative breast carcinoma | $1 \times 10^{-6}$ |
| 21-MT-1 | ER negative breast carcinoma | $2 \times 10^{-7}$ |
| 21-MT-2 | ER negative breast carcinoma | $3 \times 10^{-7}$ |
| 21-NT | ER negative breast carcinoma | $1 \times 10^{-6}$ |
| 21-PT | ER negative breast carcinoma | $3 \times 10^{-7}$ |
| THP-1 | Monocytic leukemia | $5 \times 10^{-8}$ |
| U937 | Monocytic leukemia | $2 \times 10^{-7}$ |
| HL-60 | Myelocytic leukemia | $1 \times 10^{-7}$ |
| NB4 | Promyelocytic leukemia | $4 \times 10^{-8}$ |
| AML193 | Acute myelocytic leukemia | $4 \times 10^{-7}$ |
| KG-1 | Acute myeloid leukemia | $2 \times 10^{-7}$ |
| ML-1 | Myeloblastic leukemia | $1 \times 10^{-7}$ |
| NT2/D1 | Embryonal carcinoma | $1 \times 10^{-7}$ |
| A2058 | Melanoma | $2 \times 10^{-7}$ |
| MDA-MB-468[a] | ER negative breast carcinoma | $2 \times 10^{-7}$ |
| SW626[a] | Ovarian carcinoma | $3 \times 10^{-7}$ |
| AsPc-1[a] | Pancreatic carcinoma | $1 \times 10^{-7}$ |
| CAPAN-1[a] | Pancreatic carcinoma | $3 \times 10^{-7}$ |

All cells were obtained from ATCC, except as noted. They were grown under standard conditions in either DMEM, DMEM/F12, or RPMI 1640 media plus 5–10% FBS. CDDO, over the dose range $10^{-6}$ to $10^{-10}$ M, was added to cultures at the time of seeding. Three or 4 days later, cells were treated with $^3$H-thymidine for 2 h (12 h in the case of leukemia cells), and then incorporation was measured. "ER" means estrogen receptor. $^\alpha$ These cells all haveSmad4/DPC4 mutations (Schutte et al. 1996).

EXAMPLE 4

CDDO Blocks De Novo Synthesis of iNOS and COX-2

CDDO is highly active in blocking the ability of several inflammatory cytokines to induce de novo formation of the enzymes, iNOS and COX-2 (FIG. 14). FIG. 14(A) illustrates Western blots; primary mouse macrophages; IFN-γ, 10 ng/ml; LPS, 2 ng/ml were added to cultures together with triterpenoids or dexamethasone (concentrations shown as μM); cells were harvested at 12 h. FIG. 14(B) illustrates Northern blots, RAW 264.7 macrophage-like cell line. IFN-γ, 10 ng/ml; LPS, 1 ng/ml; TNF-α, 10 ng/ml, were added to cultures together with CDDO or dexamethasone. RNA prepared after 12 h; GAPDH used as a loading control. FIG. 14(C) illustrates suppression of production of NO and $PGE_2$ in primary macrophages. For NO studies, cells were treated with IFN-γ, 10 ng/ml, together with CDDO (■), dexamethasone (○), TP-82 (□), or oleanolic acid (▼). After 48 h, supernatants were analyzed for NO by the Griess reaction. For $PGE_2$ studies, cells were treated with IFN-γ, 5 ng/ml, and LPS, 5 ng/ml, together with the same set of inhibitors. After 48 h, PGE was measured in supernatants by immunoassay. Control values (no inhibition) for NO and $PGE_2$ were 4.7 nmol/2×10$^5$ cells and 2.2 ng/ml/2×10$^5$ cells, respectively. FIGS. (14D) and (14E) illustrate (human colon myofibroblasts) $^{18}$Co cells grown in MEM/10% FBS; other methods are the same as reported above for macrophages. FIG. 14(D) illustrates Northern blots showing dose-response for suppression of COX-2 mRNA after induction with IL-1β (30 pg/ml). CDDO was added together with IL-1. In FIG. (E), Western blots show suppression of COX-2 protein; CDDO was added together with IL-1β (30 pg/ml). Also shown is suppression of cumulative production of $PGE_2$ in cell supernatants by CDDO.

These effects of CDDO have been seen in primary mouse macrophages, a mouse macrophage-like tumor cell line (RAW 264.7), and in non-neoplastic human colon fibroblasts. FIG. 14A shows Western blots for expression of iNOS and COX-2 protein in primary macrophages. Neither iNOS nor COX-2 expression can be detected in these cells until they are stimulated by an inflammatory mediator such as IFN-γ or LPS. CDDO at concentrations of 1 μM or less blocked expression of both iNOS and COX-2 protein. The importance of the nitrile function at C-2 of CDDO, as seen above in FIG. 13, is again shown in FIG. 14A. FIG. 14B shows Northern blots indicating that CDDO ($10^{-6}$ M) lowered levels of mRNA expression for both iNOS and COX-2 in RAW 264.7 cells by greater than 75%. The above effects on iNOS and COX-2 are also reflected in the cumulative production of their respective enzyme products, NO and $PGE_2$, as measured in primary macrophages (FIG. 14C). Significant inhibition by CDDO was found at levels as low as $10^{-9}$ M, and again it was markedly more active than TP-82 or oleanolic acid. However, CDDO is not a direct inhibitor of the enzymatic activity of either iNOS or COX-2, since it has no immediate effect on NO or prostaglandin production if it is added to RAW cells in which synthesis of these two enzymes has already been induced (data not shown). Likewise, the actions of CDDO are not blocked by the glucocorticoid antagonist, RU-486, which is known to bind to the glucocorticoid receptor (data not shown). In these regards, CDDO is identical to the other oleanolic acid derivatives previously studied (Suh et al., 1998).

A second type of cell in which CDDO is a highly effective inhibitor of the de novo formation of COX-2 is the colon myofibroblast. These cells were selected because of the importance of stromal cell COX-2 in colon carcinogenesis (Oshima et al., 1996). CDDO blocked induction of COX-2 mRNA and protein caused by treatment of non-neoplastic $^{18}$Co cells with IL-1 (FIGS. 14D, E); again, this action was reflected in a lowering of $PGE_2$ levels in the culture medium. Although CDDO effectively blocks the induction of COX-2 by agents such as IFN-γ, LPS, TNF-α, and IL-1, CDDO is ineffective when TPA is used as the inducer of COX-2. This has been seen in 18Co cells, as well as in the human mammary epithelial cell line, 184B5/HER (Zhai et al., 1993).

EXAMPLE 5

CDDO Suppresses iNOS and Protects Against Cell Death in Rat Brain Cells

The roles of inflammatory mediators, as well as aberrant programs for cell survival and apoptosis, in the genesis of cancer and Alzheimer's Disease are now undergoing serious investigation (McGeer and McGeer, 1995; Merrill and Benveniste, 1996; Akama et al., 1998). CDDO was tested in this example as a suppressor of de novo formation of iNOS in cultured microglia (the resident macrophages of the brain), as well as its ability to protect cultured hippocampal neurons from cell death induced by P-amyloid. It was found that CDDO acts in primary microglial cultures in a manner similar to that reported above for primary peritoneal macrophages. Thus, LPS (5 ng/ml) induced iNOS in primary microglial cultures and caused a 27-fold increase in production of NO within 18 h. Concomitant treatment of these cultures with CDDO at either $10^{-6}$ or $10^{-7}$ M inhibited this induction by 73% and 52%, respectively. We have also explored the possibility that CDDO can protect cultured hippocampal neurons from cell death induced by the peptide β-amyloid, since NO has been implicated (Akama et al., 1998) in the neurotoxic actions of this peptide which is central to the pathogenesis of Alzheimer's disease (Selkoe, 1997). Hippocampal neurons were isolated and cultured from 16 day rat embryos and then treated with CDDO for 24 h before adding the β-amyloid peptide fragment, amino acids 25–35, at a final concentration of 10 μM. This dosing with β-amyloid alone caused death of more than half of the neurons in the culture within 24 h, as measured by MTT assay. However, pretreatment of the neuronal cultures with CDDO ($10^{-8}$ and $10^{-7}$ M) totally prevented this cell death, and some protective activity of CDDO was found at doses as low as $10^{-10}$ M.

SUMMARY

As seen above, compounds of the invention such as CDDO are potent, multifunctional molecules having a wide range of actions, many of them potentially useful for prevention or treatment of diseases such as cancer. Proliferation of many human tumor cell lines, including those derived from estrogen receptor-positive and -negative breast carcinomas, myeloid leukemias, and several carcinomas that bear a Smad-4 mutation are inhibited. The ability of various inflammatory cytokines, such as interferon-γ, interleukin-1, or tumor necrosis factor-α to induce de novo formation of the enzymes, inducible nitric oxide synthase (iNOS) or inducible cyclooxygenase (COX-2) in either mouse peritoneal macrophages, rat brain microglia, or human colon fibroblasts is suppressed. Also, brain hippocampal neurons are protected from cell death induced by β-amyloid. The above indicates that the compounds of the invention, e.g., CDDO, are useful in vivo, either for chemoprevention or chemotherapy of malignancy, as well as for neuroprotection.

EQUIVALENTS

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

What is claimed is:

1. A method of treating a disorder selected from cancer, neurodegenerative diseases, and inflammatory diseases, comprising administering to said subject a pharmaceutically effective amount of a composition having the formula:

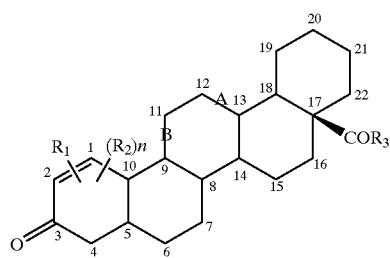

wherein either A or B is a double bond such that when A is a double bond, $C_{11}$ has substituted thereon =X, which is an organic or inorganic moiety and when B is a double bond, $C_{12}$ has substituted thereon =X, which is an organic or inorganic moiety; $R_1$ is an organic or inorganic moiety which may be substituted anywhere on the six-membered ring denoted by positions 1 through 10; $R_2$ and $R_3$ are hydrogen or organic or inorganic moieties, wherein an $R_2$ group may be substituted anywhere on the structure represented in formula (I); and n is a number from 0 to 100, such that said disorder is treated.

2. The method of claim 1, wherein said inflammatory diseases include inflammatory bowel diseases and rheumatoid arthritis.

3. The method of claim 2 wherein said neurodegenerative disease is selected from the group consisting of Parkinson's disease, Alzheimer's disease, multiple sclerosis, and amyotrophic lateral sclerosis.

4. The method of claim 2 wherein said cancer is selected from the group consisting of breast cancer, prostate cancer, colon cancer, brain cancer, and bone cancer.

5. The method of claim 1 wherein said subject is a mammal.

6. The method of claim 1 wherein said subject is a human.

7. The method of claim 1 wherein $R_1$ is a cyano group.

8. The method of claim 1 wherein B is a double bond, X is O, $R_3$ is —OH, and $R_1$ is a cyano group.

9. The method of claim 1 wherein said composition is selected from the group consisting of 3,11-dioxoolean-1,12-dien-28oic acid, 2-cyano-3,11-dioxoolean-1,12-dien-28oic acid and 2-cyano-3,12-dioxoolean-1,9-dien-28oic acid.

10. The method of claim 1 wherein $R_1$ is selected from the group consisting of cyano, halo, or —OR' wherein R' is H or an organic moiety.

11. The method of claim 1 wherein $R_1$ is an electron-withdrawing moiety.

12. The method of claim 2, wherein said inflammatory bowel diseases includes Crohn's disease and ulcerative colitis.

13. A method of inhibiting interferon γ-induced nitric oxide production in cells of a subject, comprising administering to said subject a pharmaceutically effective amount of a composition having the formula:

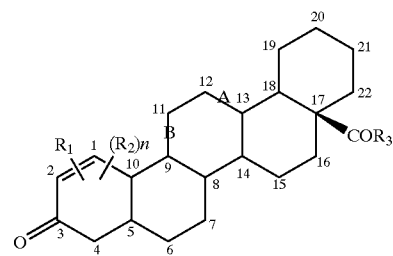

wherein either A or B is a double bond such that when A is a double bond, $C_{11}$ has substituted thereon =X, which is an organic or inorganic moiety and when B is a double bond, $C_{12}$ has substituted thereon =X, which is an organic or inorganic moiety; $R_1$ is an organic or inorganic moiety which may be substituted anywhere on the six-membered ring denoted by positions 1 through 10; $R_2$ and $R_3$ are hydrogen or organic or inorganic moieties, wherein an $R_2$ group may be substituted anywhere on the structure represented in formula (I); and n is a number from 0 to 100, such that said nitric oxide production is inhibited.

14. The method of claim 12 wherein $R_1$ is a cyano group.

15. The method of claim 13 wherein B is a double bond, X is O, $R_3$ is —OH, and $R_1$ is a cyano group.

16. The method of claim 13 wherein said composition is selected from the group consisting of 3,11-dioxoolean-1,12-dien-28oic acid, 2-cyano-3,11-dioxoolean-1,12-dien-28oic acid and 2-cyano-3,12-dioxoolean-1,9-dien-28oic acid.

17. The method of claim 13 wherein $R_1$ is selected from the group consisting of cyano, halo, or —OR' wherein R' is H or an organic moiety.

18. The method of claim 13 wherein $R_1$ is an electron-withdrawing moiety.

19. The method of claim 18 wherein $R_1$ is at position 2.

20. The method of claim 13 wherein said composition has the formula:

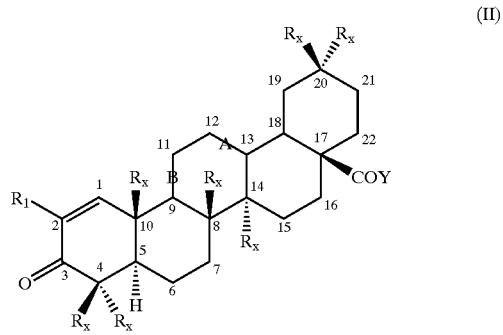

(II)

wherein $R_x$ represents an organic or inorganic moiety.

21. The method of claim 20, wherein $R_x$ is methyl.

22. The method of claim 21, wherein Y is hydroxyl.

23. A method of decreasing transcription of iNOS or COX-2 genes, comprising administering to a subject a pharmaceutically effective amount of a composition having the formula:

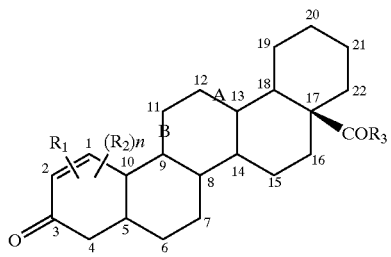

wherein either A or B is a double bond such that when A is a double bond, $C_{11}$ has substituted thereon =X, which is an organic or inorganic moiety and when B is a double bond, $C_{12}$ has substituted thereon =X, which is an organic or inorganic moiety; $R_1$ is an organic or inorganic moiety which may be substituted anywhere on the six-membered ring denoted by positions 1 through 10; $R_2$ and $R_3$ are hydrogen or organic or inorganic moieties, wherein an $R_2$ group may be substituted anywhere on the structure represented in formula (I); and n is a number from 0 to 100, such that transcription of said iNOS or COX-2 genes is decreased.

24. The method of claim 23 wherein $R_1$ is a cyano group.

25. The method of claim 23 wherein B is a double bond, X is O, $R_3$ is —OH, and $R_1$ is a cyano group.

26. The method of claim 23 wherein said composition is selected from the group consisting of 3,11-dioxoolean-1,12-dien-28oic acid, 2-cyano-3,11-dioxoolean-1,12-dien-28oic acid and 2-cyano-3,12-dioxoolean-1,9-dien-28oic acid.

27. The method of claim 23 wherein $R_1$ is selected from the group consisting of cyano, halo, or —OR' wherein R' is H or an organic moiety.

28. The method of claim 23 wherein $R_1$ is an electron-withdrawing moiety.

29. The method of claim 28 wherein said electron-withdrawing moiety is selected from the group consisting of cyano, aryl, and halosubstituted alkyl moieties.

30. The method of claim 23 wherein said composition has the formula:

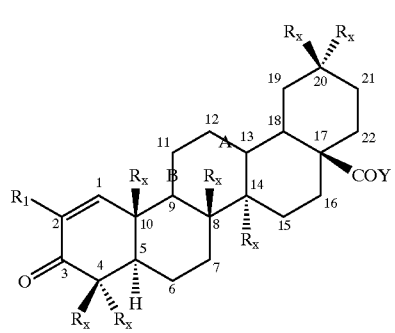

wherein $R_x$ represents an organic or inorganic moiety.

31. The method of claim 30 wherein $R_x$ is methyl.

32. The method of claim 31 wherein Y is hydroxyl.

33. A method of treating a neurodegenerative disease, comprising administering to a subject a pharmaceutically effective amount of a composition having the formula:

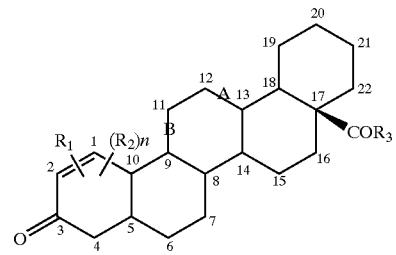

wherein either A or B is a double bond such that when A is a double bond, $C_{11}$ has substituted thereon =X, which is an organic or inorganic moiety and when B is a double bond, $C_{12}$ has substituted thereon =X, which is an organic or inorganic moiety; $R_1$ is an organic or inorganic moiety which may be substituted anywhere on the six-membered ring denoted by positions 1 through 10; $R_2$ and $R_3$ are hydrogen or organic or inorganic moieties, wherein an $R_2$ group may be substituted anywhere on the structure represented in formula (I); and n is a number from 0 to 100, such that said neurodegenerative disease is treated in said subject.

34. The method of claim 33 wherein said neurodegenerative disease is selected from the group consisting of Parkinson's disease, Alzheimer's disease, multiple sclerosis, and amyotrophic lateral sclerosis.

35. The method of claim 33 wherein said subject is a mammal.

36. The method of claim 33 wherein said subject is a human.

37. The method of claim 33 wherein $R_1$ is a cyano group.

38. The method of claim 33 wherein B is a double bond, X is O, $R_3$ is —OH, and $R_1$ is a cyano group.

39. The method of claim 33 wherein said composition is selected from the group consisting of 3,11-dioxoolean-1,12-dien-28oic acid, 2-cyano-3,11-dioxoolean-1,12-dien-28oic acid and 2-cyano-3,12-dioxoolean-1,9-dien-28oic acid.

40. The method of claim 33 wherein $R_1$ is selected from the group consisting of cyano, halo, or —OR' wherein R' is H or an organic moiety.

41. The method of claim 33 wherein $R_1$ is an electron-withdrawing moiety.

42. The method of claim 41 wherein $R_1$ is at position 2.

43. The method of claim 41 wherein said composition has the formula:

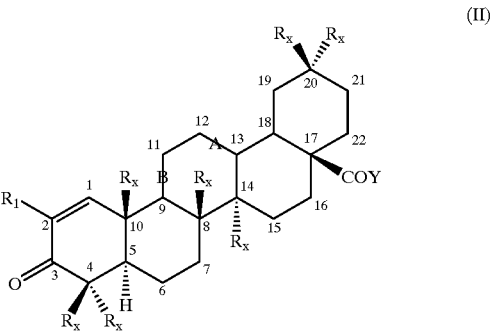

wherein $R_x$ represents an organic or inorganic moiety.

44. The method of claim 43 wherein $R_x$ is methyl.

45. The method of claim 44 wherein Y is hydroxyl.

46. A method of treating a disorder characterized by overexpression of iNOS or COX-2 genes, comprising administering to a subject a pharmaceutically effective amount of a composition having the formula:

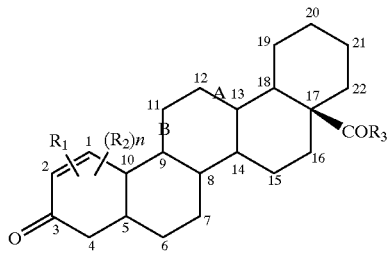

wherein A or B is a single or double bond and $C_{11}$ or $C_{12}$ have substituted thereon =X, which is an organic or inorganic moiety; $R_1$ is an organic or inorganic moiety which may be substituted anywhere on the six-membered ring denoted by positions 1 through 10; $R_2$ and $R_3$ are hydrogen or organic or inorganic moieties, wherein an $R_2$ group may be substituted anywhere on the structure represented in formula (I); and n is a number from 0 to 100, such that said disorder is treated.

47. A method for treating a condition in a subject caused by activated macrophages comprising administering to the a compound having the formula:

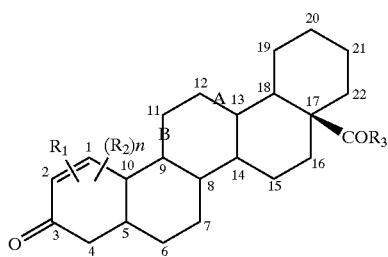

wherein either A or B is a double bond such that when A is a double bond, $C_{11}$ has substituted thereon =X, which is an organic or inorganic moiety and when B is a double bond, $C_{12}$ has substituted thereon =X, which is an organic or inorganic moiety; $R_1$ is an organic or inorganic moiety which may be substituted anywhere on the six-membered ring denoted by positions 1 through 10; $R_2$ and $R_3$ are hydrogen or organic or inorganic moieties, wherein an $R_2$ group may be substituted anywhere on the structure represented in formula (I); and n is a number from 0 to 100; and wherein said compound is dispersed in a pharmaceutically effective carrier in an amount effective to decrease macrophage activity, thereby treating the condition.

48. The method of claim 47, wherein the compound is CDDO.

49. A method of treating a disorder characterized by overexpression of iNOS or COX-2 genes, comprising administering to a subject a pharmaceutically effective amount of a composition having the formula:

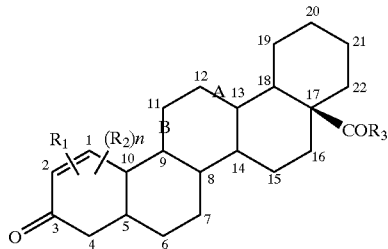

wherein either A or B is a double bond such that when A is a double bond, $C_{11}$ has substituted thereon =X, which is an organic or inorganic moiety and when B is a double bond, $C_{12}$ has substituted thereon =X, which is an organic or inorganic moiety; $R_1$ is an organic or inorganic moiety which may be substituted anywhere on the six-membered ring denoted by positions 1 through 10; $R_2$ and $R_3$ are hydrogen or organic or inorganic moieties, wherein an $R_2$ group may be substituted anywhere on the structure represented in formula (I); and n is a number from 0 to 100, such that the disorder is treated.

50. The method of claim 49 wherein said disorder is selected from the group consisting of cancer, neurodegenerative diseases, and rheumatoid arthritis.

51. The method of claim 50 wherein said neurodegenerative disease is selected from the group consisting of Parkinson's disease, Alzheimer's disease, multiple sclerosis, and amyotrophic lateral sclerosis.

52. The method of claim 50 wherein said cancer is selected from the group consisting of breast cancer, prostate cancer, colon cancer, brain cancer, and bone cancer.

53. The method of claim 49 wherein said subject is a mammal.

54. The method of claim 49 wherein said subject is a human.

55. The method of claim 49 wherein $R_1$ is a cyano group.

56. The method of claim 49 wherein B is a double bond, X is O, $R_3$ is —OH, and $R_1$ is a cyano group.

57. The method of claim 49 wherein said composition is selected from the group consisting of 3,11-dioxoolean-1,12-dien-28oic acid, 2-cyano-3,11-dioxoolean-1,12-dien-28oic acid and 2-cyano-3,12-dioxoolean-1,9-dien-28oic acid.

58. The method of claim 49 wherein $R_1$ is selected from the group consisting of cyano, halo, or —OR' wherein R' is H or an organic moiety.

59. The method of claim 49 wherein $R_1$ is an electron-withdrawing moiety.

60. The method of claim 59 wherein $R_1$ is at position 2.

61. The method of claim 2, wherein said neurodegenerative diseases includes Parkinson's disease, Alzheimer's disease, multiple sclerosis and amyotrophic lateral sclerosis.

* * * * *

UNITED STATES PATENT AND TRADEMARK OFFICE
CERTIFICATE OF CORRECTION

| | | |
|---|---|---|
| PATENT NO. | : 6,552,075 B1 | Page 1 of 1 |
| APPLICATION NO. | : 09/927081 | |
| DATED | : April 22, 2003 | |
| INVENTOR(S) | : Gordon W. Gribble et al. | |

It is certified that error appears in the above-identified patent and that said Letters Patent is hereby corrected as shown below:

In claim 3, column 19, line 48, delete "2" and insert --1-- therefor.

In claim 4, column 19, line 52, delete "2" and insert --1-- therefor.

In claim 14, column 20, line 33, delete "12" and insert --13-- therefor.

In claim 61, column 24, lines 53-55, delete all of claim 61.

Signed and Sealed this

Twenty-fifth Day of March, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,552,075 B2 | Page 1 of 1 |
| APPLICATION NO. | : 09/927081 | |
| DATED | : April 22, 2003 | |
| INVENTOR(S) | : Gordon W. Gribble et al. | |

It is certified that error appears in the above-identified patent and that said Letters Patent is hereby corrected as shown below:

In column 1, lines 12-16, delete paragraph and insert
--This invention was made with government support under grant numbers CA-23108, RO1 CA 54494, RO1 CA 62275, KO1 CA 75154, NS 28767 awarded by the National Institutes of Health, and DOD/AMRD award number 1796-1-6163 awarded by the Department of Defense. The government has certain rights in the invention.-- therefor.

Signed and Sealed this

Twentieth Day of December, 2011

David J. Kappos
*Director of the United States Patent and Trademark Office*